United States Patent
Cummings et al.

(10) Patent No.: US 6,984,261 B2
(45) Date of Patent: Jan. 10, 2006

(54) USE OF CERAMICS IN DENTAL AND ORTHODONTIC APPLICATIONS

(75) Inventors: Kevin M. Cummings, Little Canada, MN (US); Jacqueline C. Rolf, River Falls, WI (US); Anatoly Z. Rosenflanz, Maplewood, MN (US); Richard P. Rusin, Woodbury, MN (US); Jerome E. Swanson, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/358,856

(22) Filed: Feb. 5, 2003

(65) Prior Publication Data

US 2004/0152034 A1 Aug. 5, 2004

(51) Int. Cl.
*A61K 6/00* (2006.01)

(52) U.S. Cl. .................. 106/35; 433/8; 433/9; 433/17; 433/206; 433/215; 433/218; 433/201.1; 433/202.1; 433/222.1; 501/153; 501/152; 501/127; 501/105; 501/1; 501/2; 501/3; 501/4; 501/5; 501/6; 501/7; 501/8; 501/9; 501/10; 501/41; 501/42; 501/43; 501/44; 501/45; 501/46; 501/47; 501/48; 501/49; 501/50; 501/51; 501/52; 501/73; 501/74; 501/75; 501/76; 501/77; 501/78; 501/79

(58) Field of Classification Search .............. 501/1–10, 501/41–52, 73–79, 105, 127, 152, 153; 106/35; 433/8, 9, 17, 215, 218, 206, 202.1, 201.1, 433/222.1
See application file for complete search history.

(56) References Cited

U.S. PATENT DOCUMENTS

| | | | |
|---|---|---|---|
| 906,339 A | 12/1908 | Tone |
| 1,037,999 A | 9/1912 | Saunders |
| 1,161,620 A | 11/1915 | Coulter |
| 1,192,709 A | 7/1916 | Tone |

(Continued)

FOREIGN PATENT DOCUMENTS

| | | |
|---|---|---|
| DE | 2 034 011 | 1/1972 |
| EP | 0 173 567 A2 | 3/1986 |

(Continued)

OTHER PUBLICATIONS

"A ductile ceramic eutectic composite with high strength at 1,873 K", Waku et al., Nature, vol. 389, Sep. 4, 1997, pp. 49–52.
"Advances in the Grinding Efficiency of Sintered Alumina Abrasives," Krell et al., J. Am. Ceram. Soc., 79 [3], 1996, pp. 763–769.

(Continued)

*Primary Examiner*—C. Melissa Koslow

(57) ABSTRACT

The invention relates to uses of glasses and glass-ceramics in dental and orthodontic applications.

8 Claims, 3 Drawing Sheets

U.S. PATENT DOCUMENTS

| | | |
|---|---|---|
| 1,240,490 A | 9/1917 | Saunders et al. |
| 1,263,708 A | 4/1918 | Saunders et al. |
| 2,618,567 A | 11/1952 | Comstock |
| 3,066,112 A | 11/1962 | Bowen |
| 3,181,939 A | 5/1965 | Marshall et al. |
| 3,539,533 A | 11/1970 | Lee, II et al. |
| 3,629,187 A | 12/1971 | Walier |
| 3,708,296 A | 1/1973 | Schlesinger |
| 3,709,866 A | 1/1973 | Waller |
| 3,714,059 A | 1/1973 | Shaw et al. |
| 3,717,583 A | 2/1973 | Shaw et al. |
| 3,751,399 A | 8/1973 | Lee, Jr. et al. |
| 3,754,978 A | 8/1973 | Elmer et al. |
| 3,766,132 A | 10/1973 | Lee, Jr. et al. |
| 3,860,556 A | 1/1975 | Taylor |
| 3,881,282 A | 5/1975 | Watson |
| 4,002,669 A | 1/1977 | Gross et al. |
| 4,069,055 A | 1/1978 | Crivello |
| 4,071,424 A | 1/1978 | Dart et al. |
| 4,111,707 A | 9/1978 | Komorita et al. |
| 4,115,346 A | 9/1978 | Gross et al. |
| 4,182,437 A | 1/1980 | Roberts et al. |
| 4,216,288 A | 8/1980 | Crivello |
| 4,217,264 A | 8/1980 | Mabie et al. |
| 4,250,311 A | 2/1981 | Crivello |
| 4,259,117 A | 3/1981 | Yamauchi et al. |
| 4,292,029 A | 9/1981 | Craig et al. |
| 4,308,190 A | 12/1981 | Walkowiak et al. |
| 4,327,014 A | 4/1982 | Kawahara et al. |
| 4,379,695 A | 4/1983 | Orlowski et al. |
| 4,387,240 A | 6/1983 | Berg |
| 4,404,150 A | 9/1983 | Tsunekawa et al. |
| 4,415,510 A | 11/1983 | Richmond |
| 4,503,169 A | 3/1985 | Randklev |
| 4,530,909 A | 7/1985 | Makishima et al. |
| 4,552,199 A | 11/1985 | Onoyama et al. |
| 4,595,663 A | 6/1986 | Krohn et al. |
| 4,642,126 A | 2/1987 | Zador et al. |
| 4,652,274 A | 3/1987 | Boettcher et al. |
| 4,737,593 A | 4/1988 | Ellrich et al. |
| 4,762,677 A | 8/1988 | Dolgin |
| 4,770,671 A | 9/1988 | Monroe et al. |
| 4,772,436 A | 9/1988 | Tyszblat |
| 4,772,511 A | 9/1988 | Wood et al. |
| 4,772,530 A | 9/1988 | Gottschalk et al. |
| 4,789,501 A | 12/1988 | Day et al. |
| 4,820,666 A | 4/1989 | Hirano et al. |
| 4,874,450 A | 10/1989 | Gottschalk |
| 4,950,294 A | 8/1990 | Hakamatsuka |
| 4,954,414 A | 9/1990 | Adair et al. |
| 4,985,340 A | 1/1991 | Palazzotto et al. |
| 5,055,372 A | 10/1991 | Shanklin et al. |
| 5,057,018 A | 10/1991 | Bowen |
| 5,057,393 A | 10/1991 | Shanklin et al. |
| 5,084,586 A | 1/1992 | Farooq |
| 5,089,536 A | 2/1992 | Palazzotto |
| 5,104,319 A | 4/1992 | Evans et al. |
| 5,124,417 A | 6/1992 | Farooq |
| 5,130,347 A | 7/1992 | Mitra |
| 5,131,926 A | 7/1992 | Rostoker et al. |
| 5,185,299 A | 2/1993 | Wood et al. |
| 5,215,563 A | 6/1993 | LaCourse et al. |
| 5,227,104 A | 7/1993 | Bauer |
| 5,250,352 A | 10/1993 | Tyszblat |
| 5,332,429 A | 7/1994 | Mitra et al. |
| 5,498,269 A | 3/1996 | Larmie |
| 5,534,843 A | 7/1996 | Tsunoda et al. |
| 5,545,676 A | 8/1996 | Palazzotto et al. |
| 5,605,870 A | 2/1997 | Strom-Olsen et al. |
| 5,641,469 A | 6/1997 | Garg et al. |
| 5,665,127 A | 9/1997 | Moltgen et al. |
| 5,693,239 A | 12/1997 | Wang et al. |
| 5,733,564 A | 3/1998 | Lehtinen |
| 5,747,397 A | 5/1998 | McPherson et al. |
| 5,804,513 A | 9/1998 | Sakatani et al. |
| 5,856,373 A | 1/1999 | Kaisaki et al. |
| 5,902,763 A | 5/1999 | Waku et al. |
| 5,910,273 A | 6/1999 | Thiel et al. |
| 5,916,498 A | 6/1999 | Hofmann et al. |
| 5,958,361 A | 9/1999 | Laine et al. |
| 5,976,274 A | 11/1999 | Inoue et al. |
| 5,981,415 A | 11/1999 | Waku et al. |
| 6,020,528 A | 2/2000 | Leppard et al. |
| 6,025,406 A | 2/2000 | Oxman et al. |
| 6,136,885 A | 10/2000 | Rusin et al. |
| 6,146,244 A | 11/2000 | Atsugi et al. |
| 6,251,813 B1 | 6/2001 | Sato |
| 6,254,981 B1 | 7/2001 | Castle |
| 6,306,926 B1 | 10/2001 | Bretscher et al. |
| 6,342,458 B1 | 1/2002 | Schweiger et al. |
| 6,362,119 B1 | 3/2002 | Chiba |
| 6,394,880 B1 | 5/2002 | Basler et al. |
| 6,398,990 B1 | 6/2002 | Evans et al. |
| 6,451,077 B1 | 9/2002 | Rosenflanz |
| 6,454,822 B1 | 9/2002 | Rosenflanz |
| 6,458,731 B1 | 10/2002 | Rosenflanz |
| 6,465,106 B1 | 10/2002 | Petticrew |
| 6,482,758 B1 | 11/2002 | Weber et al. |
| 6,511,739 B2 | 1/2003 | Kasai et al. |
| 6,648,638 B2 * | 11/2003 | Castro et al. ............. 433/8 |
| 2003/0110708 A1 * | 6/2003 | Rosenflanz ............. 51/307 |
| 2003/0126803 A1 * | 7/2003 | Rosenflanz ............. 51/307 |
| 2003/0126804 A1 * | 7/2003 | Rosenflanz et al. ...... 51/307 |
| 2003/0145525 A1 * | 8/2003 | Rosenflanz ............. 51/307 |

FOREIGN PATENT DOCUMENTS

| | | |
|---|---|---|
| EP | 0 647 601 A1 | 4/1995 |
| EP | 0 705 803 A1 | 4/1996 |
| EP | 0 709 347 A1 | 5/1996 |
| EP | 0 716 049 A2 | 6/1996 |
| EP | 0 722 919 A1 | 7/1996 |
| EP | 0 291 029 B2 | 11/1996 |
| GB | 1 260 933 | 1/1972 |
| JP | 60-221338 | 11/1985 |
| JP | 63-156024 | 6/1988 |
| JP | 63-303821 | 12/1988 |
| JP | 4-119941 | 4/1992 |
| JP | 6-40765 | 2/1994 |
| JP | 11-189926 | 7/1999 |
| JP | 2000-45128 | 2/2000 |
| JP | 2000-45129 | 2/2000 |
| JP | 2001-294480 | 10/2001 |
| SU | 1455569 | 7/1996 |
| WO | WO 97/16385 | 5/1997 |
| WO | WO 01/09992 A2 | 2/2001 |
| WO | WO 01/13862 A1 | 3/2001 |
| WO | WO 01/16047 A2 | 3/2001 |
| WO | WO 01/27046 A1 | 4/2001 |
| WO | WO 01/30306 A1 | 5/2001 |
| WO | WO 02/08146 A1 | 1/2002 |
| WO | WO 02/085313 A1 | 10/2002 |
| WO | WO 03/011781 A2 | 2/2003 |
| WO | WO 2004/013058 A1 | 2/2004 |
| WO | WO 2004/016821 A2 | 2/2004 |

OTHER PUBLICATIONS

"A jelly-like ceramic fiber at 1193 K", Waku et al., Mat Res Innovat (2000) 3, pp. 185–189.

"A New Ceramic Eutectic Composite with High Strength at 1873 K", Waku, Adv. Mater., 1998, 10, No. 8, pp. 615–617.

"Aspects of Synthesis of Decorite Opacified Glass", Kondrashov et al., Glass and Ceramics, vol. 58, Nos. 1–2, 2001, pp. 8–11.
"China: Oversupply puts rare earths projects on hold", Industrial Minerals, Aug., 1997.
"China Rare Earth Information", China Rare Earth Information Center, vol. 6, No. 4, Aug. 2000.
"China's Rare Earth Export Quota Set at 45,000 Tons", Dow Jones Interactive Internet Printout on Jun. 20, 2001, http://ptg.djnr.com/ccroot/asp/publib/story.asp.
"China's Rare Earth Industry In the Doldrums", Dow Jones Interactive Internet Printout on Jun. 20, 2001, http://ptg.djnr.com/ccroot/asp/publib/story.asp.
"Crystallization and thermal properties of $Al_2O_3$–$Y_2O_3$ melts", Stankus et al., Elsevier, Journal of Crystal Growth 167 (1996), pp. 165–170.
"Device materials based on Er–, Ho–, Tm–, and Yb–doped rare earth aluminum oxide (REAl™) glass", Weber et al., Containerless Research, Inc. (Believed to be presented at Optoelectronics 2003 Conference, Jan. 30, 2003).
"Divorced eutectic and interface characteristics in a solidified YAG–spinel composite with spinel–rich composition", Wang et al., Journal of Materials Science 35 (2000), pp. 2757–2761.
"Durable 3–5 $\mu$m transmitting infrared window materials" Harris, Elsevier, Infrared Physics & Technology, 39, 1998, pp. 185–201.
"Elements: China to impose quotas on rare earth exports", Dow Jones Interactive Internet Printout on Jun. 20, 2001, http://ptg.djnr.com/ccroot/asp/publib/story.asp.
"Erbium–doped phosphate glass waveguide on silicon with 4.1 dB/cm gain at 1.535 $\mu$m", Yan et al., Appl. Phys. Lett, 71 (20), Nov. 17, 1997, pp. 2922–2924.
"Eutectic Precipitation of the Spinel Solid Solution–Yttrium–Aluminum Garnet (YAG) System," Wang et al., J. Am. Ceram. Soc., 81 [1], 1998, pp. 263–265.
"$Gd_3Al_5O_{12}$ Phase Obtained by Crystallization of Amorphous $Gd_2O_3$ $^{5/3}Al_2O_3$", Shishido et al., Journal of the American Ceramic Society—Discussion and Notes, Jul.–Aug. 1978, pp. 373–375.
"Glass fibres of pure and erbium– or neodymium–doped yttria–alumina compositions", Weber et al., Nature, vol. 393, Jun. 25, 1998, pp. 769–771.
"Glass Formation and Polyamorphism in Rare–Earth Oxide– Aluminum Oxide Compositions", Weber et al., J. Am. Ceram. Soc., 83 [8], 2000, pp. 1868–1872.
"Glass Formation in the Ln–Al–O System (Ln: Lanthanoid and Yttrium Elements)", Chemistry Letters, Chemical Society of Japan, 1973, pp. 1327–1330.
"High–temperature strength and thermal stability of a unidirectionally solidified $Al_2O_3$/YAG eutectic composite", Waku et al., 1998 Chapman & Hall, pp. 1217–1225.
"In Asia", Dow Jones Interactive Internet Printout on Jun. 20, 2001, http://ptg.djnr.com/ccroot/asp/publib/story.asp.
"Increase in value of rare–earth products boosts Yixing Xinwei", South China Morning Post, Apr. 12, 2000.
"Interface modification for increased fracture toughness in reaction formed yttrium aluminum garnet/alumina eutectic composites," Brewer et al., J. Mater. Res., vol. 14, No. 10, Oct. 1999, pp. 3907–3912.
"Kinetics of nonisothermal sintering of some eutectic oxide compositions, "Volkova et al., 1986 (Abstract from Database Chemabs Online! Chemical Abstracts Service, Columbus, Ohio, US).

"Melt–extracted oxide ceramic fibres—the fundamentals", Allahverdi et al., 1996 Chapman & Hall, pp. 1035–1042.
"Melt extraction processing of structural $Y_2O_3$–$Al_2O_3$ fibers", Aguilar et al., Journal of the European Ceramic Society 20 (2000), pp. 1091–1098.
"Metastable Phase Relationships In the System $Al_2O_3$–$ZrO_2$–$Y_2O_3$", Lakiza et al., Powder Metallurgy and Metal Ceramics, vol. 35, Nos. 11–12, 1996, pp. 621–626.
"Methods Of Investigation Of Properties Of Powder Materials, Interactions in the $Al_2O_3$–$ZrO_2$–$Y_2O_3$ System", Lakiza et al., Powder Metallurgy and Metal Ceramics, vol. 33, Nos. 9–10, 1994, pp. 486–490.
"Microstructure and Thermal Stability of $Al_2O_3$/$Y_3Al_5O_{12}$ (YAG) Eutectic Composite Prepared by an Arc Discharge Method", Isobe et al., Journal of the Ceramic Society of Japan, 109, [1], 2001, pp. 66–70 (Abstract in English).
"Microstructures of laser–treated $Al_2O_3$–$ZrO_2$–$CeO_2$ composites," Chen et al., Elsevier, Materials Science and Engineering A196 (1995), pp. 253–260.
"Net optical gain at 1.53 $\mu$m in Er–doped $Al_2O_3$ waveguides on silicon", van den Hoven et al., Appl. Phys. Lett. 68 (14), Apr. 1, 1996, pp. 1886–1888.
"Non–stoichiometry and defect structures in rapidly solidified MgO–$Al_2O_3$–$ZrO_2$ ternary eutectics," McKittrick et al., Elsevier, Materials Science and Engineering A231 (1997), pp. 90–97.
*Phase Diagrams For Ceramists*, Figs. 311, 346, 350, 354–356, 373, and 716, The American Ceramic Society, 1964, pp. 122, 136, 138, 140, 144, 248.
*Phase Diagrams For Ceramists, 1969 Supplement*, Figs. 2340–2344, 2363, 2370, 2374–2375, 2382–2383, 2385, 2387, 2390, and 2392, The American Ceramic Society, 1969, pp. 95–96, 100, 102–103, 105–108.
*Phase Diagrams For Ceramists, 1975 Supplement*, Figs. 4366–4371, 4377–4378, 4404–4405, 4417, 4426, 4430, 4433, 4437, 4440, 4444, 4457, 4572, and 4602, The American Ceramic Society, 1975, pp. 130–132, 135–136, 147, 152, 157, 159–160, 163–164, 166, 172–173, 238, 257.
*Phase Diagrams For Ceramists, vol. IV*, Figs. 5042, 5211, 5217, 5224, 5228, 5232, 5237, 5239, 5241, 5245, 5251, 5257, 5418, and 5437, The American Ceramic Society, 1981, pp. 29, 125, 127, 129–131, 133, 135–137, 139, 141, 143, 220, 228.
*Phase Diagrams For Ceramists, vol. VI*, Fig. 6464, The American Ceramic Society, 1981, p. 162.
"Phase Equilibria in the Yttrium Oxide–Alumina System", Toropov et al., Bulletin of the Academy of Sciences, USSR, Division of Chemical Science, No. 7, Jul., 1964, pp. 1076–1081, A translation of Seriya Khimicheskaya.
*Phase Equilibria Diagrams, Phase Diagrams For Ceramists, vol. XI, Oxides*, Figs. 9261–9264, The American Ceramic Society, 1995, pp. 105–106.
"Phase identification of $Al_2O_3$/$RE_3Al_5O_{12}$ and $Al_2O_3$REAl$O_3$ (RE= Sm–Lu, Y) eutectics", Yoshikawa et al., Elsevier, Journal of Crystal Growth 218 (2000), pp. 67–73.
"Powder–Material Research Methods And Properties, Polythermal Sections Of The $Al_2O_3$–$ZrO_2$–$Y_2O_3$ Phase Diagram", Lakiza et al., Powder Metallurgy and Metal Ceramics, vol. 34, Nos. 11–12, 1995, pp. 655–659.
"Preliminary data on subsolidus phase equilibria in the $La_2O_3$–$Al_2O_3$–$Mn_2O_3$ and $La_2O_3$–$Al_2O_3$–$Fe_2O_3$ systems", Hrovat et al., Journal of Materials Science Letters 14 (1995), pp. 265–267.

"Prices", Asian Ceramics and Glass, Jan. 2001.
"Processing and crystallization of rapidly solidified $Al_2O_3$–$Y_2O_3$ fibres", Aguilar et al., British Ceramic Transactions, 2000, vol. 99, No. 6, pp. 256–259.
"Processing, Microstructure, and Strength of Alumina–YAG Eutectic Polycrystals", Mah et al., J. Am. Ceram. Soc., 83 [8], 2000, pp. 2088–2090.
"Production and Studies of Alumina Based Refractory Glass", Coutures et al., Mat. Res. Bull., vol. 10, No. 6, pp. 539–545 (1975).
"Rapid Quenching on the Binary Systems of High Temperature Oxides", Suzuki et al., Mat. Res. Bull., vol. 9, 1974, pp. 745–754.
"Rapid Solidification of Ceramics, A Technology Assessment", Brockway et al., Metals and Ceramics Information Center, MCIC Report, Jan. 1984, MCIC 84–49.
"Rare Earth—Market Confusion Inevitable Due to China's Unstable Supply", Japan Chemical Week, vol. 41, No. 2080, Jul. 6, 2000, pp. 6–7.
"Rare–earth metal prices in the USA ca. 1960 to 1994", Hedrick et al., Journal of Alloys and Compounds 250 (1997), pp. 471–481.
"Rare–Earth Metals", Hedrick, 1997, pp. 61.1–61.6.
"Rare earth oxide–aluminum oxide glasses for mid range IR devices", Weber et al., Containerless Research, Inc. (Believed to be presented at Bios 2003 Conference, Jan. 26, 2003).
"Rare earth prices and market outlook", Dow Jones Interactive Internet Printout on Jan. 20, 2001, http://ptg.djnr.com/ccroot/asp/publib/story.asp.
"Rare earths: an industry review and market outlook—part 1", Dow Jones Interactive Internet Printout on Jan. 20, 2001, http://ptg.djnr.com/ccroot/asp/publib/story.asp.
"Rare earths prices recover despite china's overcapacity", Louise Rodriquez, America Metal Market, vol. 109, No. 14, Jan. 22, 2001, p. 13.
"Sapphire matrix composites reinforced with single crystal VAG phases", Waku et al., Journal of Materials Science 31 (1996), pp. 4663–4670.
"Solidus Surface And Phase Equilibria During The Solidification Of Alloys In The $Al_2O_3$–$ZrO_2$–$Y_2O_3$ System", Lakiza et al., Powder Metallurgy and Metal Ceramics, vol. 34, Nos. 1–2, 1995, pp. 64–67.
"Synthesis of Y–Al Garnet", Krokhin et al., Glass and Ceramics, vol. 55, Nos. 5–6, 1998, pp, 151–152.
"The Liquidus Surface In The $Al_2O_3$–$ZrO_2$–$Y_2O_3$ Phase Diagram", Lakiza et al., Powder Metallurgy and Metal Ceramics, vol. 33, Nos. 11–12, 1994, pp. 595–597.
"Thermo–Mechanical Stability Of Directionally Solidified $Al_2O_3$–$ZrO_2(Y_2O_3)$ Eutectic Fibers", Yang et al., Scripta Materialia, vol. 36, No. 9, 1997, pp. 961–965.
"Traders' view on chemical business (Part 2): rare earth: market confusion inevitable due to China's unstable supply", Dow Jones Interactive Internet Printout on Jun. 20, 2001, http://ptg.djnr.com/ccroot/asp/publib/story.asp.
"Unusual Glass Formation in the Al–Nd–O System", Chemistry Letters, 1973, pp. 741–742.
U.S. Appl. No. 09/620,262, filed Jul. 19, 2000, Fused $Al_2O_3$–$Y_2O_3$ Eutectic Abrasive Particles, Abrasive Articles, And Methods Of Making And Using The Same.
U.S. Appl. No. 09/704,843, filed Nov. 2, 2000, Fused $Al_2O_3$–MgO–$Y_2O_3$ Eutectic Abrasive Particles, Abrasive Articles, And Methods Of Making And Using The Same.

U.S. Appl. No. 09/618,879, filed Jul. 19, 2000, Fused $Al_2O_3$ Rare Earth Oxide Eutectic Abrasive Particles, Abrasive Articles, And Methods Of Making And Using The Same.
U.S. Appl. No. 09/772,730, filed Jan. 30, 2001, Fused $Al_2O_3$–MgO–Rare Earth Oxide Eutectic Abrasive Particles, Abrasive Articles, And Methods Of Making And Using The Same.
U.S. Appl. No. 09/619,191, filed Jul. 19, 2000, Fused Abrasive Particles, Abrasive Articles, And Methods Of Making And Using The Same.
U.S. Appl. No. 09/619,289, filed Jul. 19, 2000, Fused Aluminum Oxycarbide/Nitride– $Al_2O_3$ Rare Earth Oxide Eutectic Abrasive Particles, Abrasive Articles, And Methods Of Making And Using The Same.
U.S. Appl. No. 09/619,106, filed Jul. 19, 2000, Fused Aluminum Oxycarbide/Nitride–$Al_2O_3$ Rare Earth Oxide Eutectic Materials.
U.S. Appl. No. 09/618,876, filed Jul. 19, 2000, Fused $Al_2O_3$–$Y_2O_3$–$ZrO_2$ Eutectic Abrasive Particles, Abrasive Articles, And Methods Of Making And Using The Same.
U.S. Appl. No. 09/619,192, filed Jul. 19, 2000, Fused $Al_2O_3$–Rare Earth Oxide $ZrO_2$ Eutectic Materials.
U.S. Appl. No. 09/619,744, filed Jul. 19, 2000, Fused $Al_2O_3$–Rare Earth Oxide–$ZrO_2$ Eutectic Abrasive Particles, Abrasive Articles, And Methods Of Making And Using The Same.
U.S. Appl. No. 10/211,597, filed Aug. 2, 2002, $Al_2O_3$–Rare Earth Oxide–$ZrO_2$/$HfO_2$ Materials, and Methods of Making and Using the Same.
U.S. Appl. No. 10/211,638, filed Aug. 2, 2000, $Al_2O_3$–$Y_2O_3$–$ZrO_2$/$HfO_2$ Materials, and Methods of Making and Using the Same.
U.S. Appl. No. 10/211,629, filed Aug. 2, 2002, Abrasive Particles, and Methods of Making and Using the Same.
U.S. Appl. No. 10/211,598, filed Aug. 2, 2002, Abrasive Particles, Abrasive Articles, and Methods of Making and Using the Same.
U.S. Appl. No. 10/211,630, filed Aug. 2, 2002, Abrasive Particles, and Methods of Making and Using the Same.
U.S. Appl. No. 10/211,639, filed Aug. 2, 2002, Method for Making Amorphous Materials and Ceramics.
U.S. Appl. No. 10/211,034, filed Aug. 2, 2002, Ceramic Materials, Abrasive Particles, Abrasive Articles, and Methods of Making and Using the Same.
U.S. Appl. No. 10/211,044, filed Aug. 2, 2002, Glass–Ceramics.
U.S. Appl. No. 10/211,628, filed Aug. 2, 2002, Alunmina-–Zirconia, and Methods of Making and Using the Same.
U.S. Appl. No. 10/211,491, filed Aug. 2, 2002, Method of Making Ceramic Articles.
U.S. Appl. No. 10/034,642, filed Dec. 28, 2001, Polycrystalline Translucent Alumina–Based Ceramic Material, Uses, and Methods.
U.S. Appl. No. 10/034,997, filed Dec. 28, 2001, Orthodontic Appliances Including Polycrystalline Alumina–Based Ceramic Material Kits, and Methods.
U.S. Appl. No. 10/211,640, filed Aug. 2, 2002, Plasma Spraying.
U.S. Appl. No. 10/211,684, filed Aug. 2, 2002, Method of Making Amorphous and Ceramics via Melt Spinning.
U.S. Appl. No. 10/358,772, filed Feb. 5, 2003, Methods of Making Ceramic Particles.

U.S. Appl. No. 10/358,765, filed Feb. 5, 2003, Methods of Making Ceramics.

U.S. Appl. No. 10/358,910, filed Feb. 5, 2003, Ceramics and Methods of Making the Same.

U.S. Appl. No. 10/358,855, filed Feb. 5, 2003, $Al_2O_3$–$La_2O_3$–$Y_2O_3$–MgO Ceramics, and Methods of Making the Same.

U.S. Appl. No. 10/358,708, filed Feb. 5, 2003, Methods of Making $Al_2O_3$–$SiO_2$ Ceramics.

U.S. Appl. No. 10/425,039, filed Apr. 28, 2003, Uses of Glasses Containing Rare Earth Oxide, Alumina, and Zirconia and Dopant in Optical Waveguides.

* cited by examiner

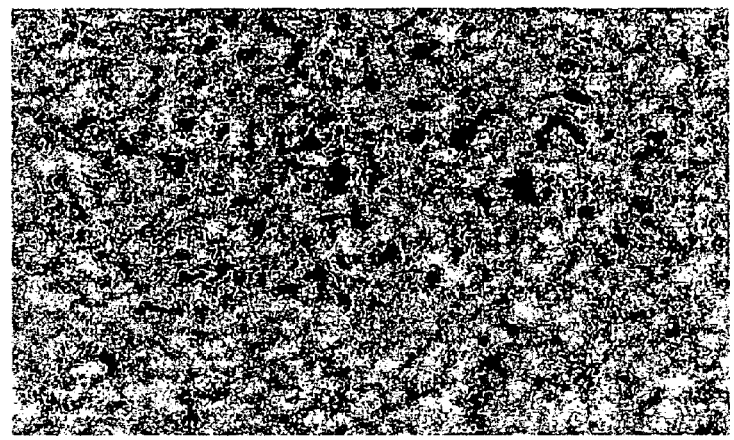
Fig. 2a  1μm
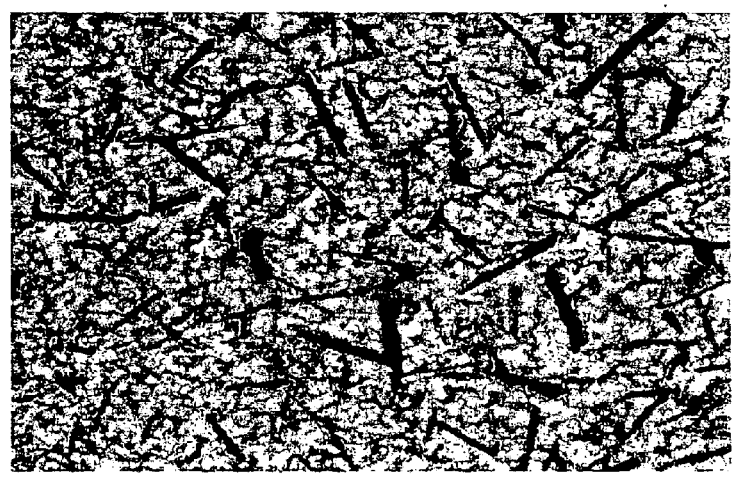
Fig. 2b  1μm

US 6,984,261 B2

USE OF CERAMICS IN DENTAL AND ORTHODONTIC APPLICATIONS

BACKGROUND

The invention relates to uses of ceramics in dental and orthodontic applications.

Although performance and durability are highly desirable characteristics for dental replacement and repair work, for example, they alone are not the sole concern for practitioners and patients. Aesthetic value, or how dental materials and articles and orthodontic appliances look inside the mouth is just as desirable.

For example, in prosthodontics and restorative dentistry, where tooth replacement or prostheses are custom made to fit in or on a tooth structure, there are instances where the restoration or repair can be seen from a short distance when the mouth is open. Thus in those instances, it would be highly desired that the dental material be nearly indistinguishable from adjacent tooth structure.

Prosthetics and restorative dentistry encompass the fabrication and installation of, for example, restoratives, replacements, inlays, onlays, veneers, full and partial crowns, bridges, implants, and posts. Conventional materials used to make dental prostheses include gold, ceramics, amalgam, porcelain, and composites. In terms of aesthetic value, it is perceived that porcelains, composites, and ceramics look better than amalgam and metals, since a prosthetic made from those nonmetals better matches or blends in with the color of adjacent natural teeth.

For orthodontic appliances (typically, brackets, which are small slotted bodies for holding a curved arch wire, and associated tooth bands if banded attachment is used), stainless steel is an ideal material because it is strong, nonabsorbent, weldable, and relatively easy to form and machine. A significant drawback of metal appliances, however, relates to cosmetic appearance when the patient smiles. Adults and older children undergoing orthodontic treatment are often embarrassed by the "metallic smile" appearance of metal bands and brackets, and this problem has led to various improvements in recent years.

One area of improvement involves use of nonmetal materials. Both plastic and ceramic materials present an improved appearance in the mouth, and often the only significantly visible metal components are thin arch wires that are cosmetically acceptable. Plastic is not an ideal material because it lacks the structural strength of metal, and is susceptible to staining and other problems. Ceramics such as sapphire or other transparent crystalline materials have undesirable prismatic effects. Also, single crystal aluminum oxide appliances are subject to cleavage under the loads that occur in the course of orthodontic treatment. Other ceramics have been largely opaque so that they either do not match tooth color or require coloring.

Glasses and glass-ceramics have also been used for dental replacement and repair work. Sinterable glass-ceramics based on lithium disilicate utilized in production of shaped dental products are known. For example, some compositions are based on $SiO_2$ (57–80 wt-%) and $Li_2O$ (11–19 wt-%) with minor amounts of $Al_2O_3$, $La_2O_3$, MgO, ZnO, $K_2O$, $P_2O_5$ and other materials. Another examples are moldable ceramic-glass compositions which include 50–99 parts by weight of alumina and/or zirconia powder and 1 to 50 parts by weight of glass powder.

Digitized machining of ceramics (commonly known as CAD/CAM milling) is one method for producing useful dental shapes. However, the machining of fully densified structural ceramics like $Al_2O_3$ and $ZrO_2$ into complex dental geometries is difficult due to rapid tool wear. For this reason, methods involving machining of green ceramic body have been developed (e.g. LAVA $ZrO_2$ by 3M Company).

SUMMARY

In one embodiment, the invention provides an article comprising a ceramic in the form of a dental article or an orthodontic appliance wherein the ceramic comprises at least one of a ceramic, glass, or glass-ceramic comprising:

a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;

b) at least 35 percent by weight $Al_2O_3$, based on the total weight of the glass or glass-ceramic, and a first metal oxide other than $Al_2O_3$, wherein the $Al_2O_3$ and the first metal oxide collectively comprise at least 70 percent by weight of the glass or glass-ceramic;

c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;

d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;

e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;

f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;

g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;

h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or i) a glass-ceramic having an average hardness of at least 13 GPa, wherein the glass-ceramic has x, y, and z dimensions each perpendicular to each other, and wherein each of the x, y, and z dimensions is at least 5 mm.

In another embodiment, the invention provides a dental material comprising a mixture of a hardenable resin and a ceramic comprising at least one of a glass or glass-ceramic comprising:

a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;

b) at least 35 percent by weight $Al_2O_3$, based on the total weight of the glass or glass-ceramic, and a first metal oxide other than $Al_2O_3$, wherein the $Al_2O_3$ and the first metal oxide collectively comprise at least 70 percent by weight of the glass or glass-ceramic;

c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;

d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;

e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;

f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;

g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;

h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or i) a glass-ceramic having an average hardness of at least 13 GPa.

In another embodiment, the invention provides a method of making a dental article or an orthodontic appliance comprising the steps of:

providing a dental or orthodontic mill blank;

carving a dental or orthodontic mill blank, wherein the mill blank comprises a glass or glass-ceramic comprising at least one of:

a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;

b) at least 35 percent by weight $Al_2O_3$, based on the total weight of the glass or glass-ceramic, and a first metal oxide other than $Al_2O_3$ wherein the $Al_2O_3$ and the first metal oxide collectively comprise at least 70 percent by weight of the glass or glass-ceramic;

c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;

d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;

e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;

f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;

g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;

h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or i) a glass-ceramic having an average hardness of at least 13 GPa.

In another embodiment, the invention provides a method of making a dental article or an orthodontic appliance comprising the steps of:

heating glass above the $T_g$ of the glass such that the glass coalesces or flows to form a dental article or an orthodontic appliance having a shape; and cooling the coalesced article, wherein the glass comprises at least one of:

a) at least 35 percent by weight $Al_2O_3$, based on the total weight of the glass, and a first metal oxide other than $Al_2O_3$, wherein the ceramic contains not more than 10 percent by weight collectively $B_2O_3$, $GeO_2$, $P_2O_5$, $SiO_2$, $TeO_2$, and $V_2O_5$, based on the total weight of the glass;

b) at least 35 percent by weight $Al_2O_3$, based on the total weight of the glass, a first metal oxide other than $Al_2O_3$, wherein the $Al_2O_3$ and the first metal oxide collectively comprise at least 70 percent by weight of the glass;

c) $Al_2O_3$ and at least one of REO or $Y_2O_3$, wherein at least 80 percent by weight of the glass collectively comprises the $Al_2O_3$ and the at least one of REO or $Y_2O_3$, based on the total weight of the glass;

d) $Al_2O_3$, at least one of REO or $Y_2O_3$, and at least one of $ZrO_2$ or $HfO_2$, wherein at least 80 percent by weight of the glass collectively comprises the $Al_2O_3$, at least one of REO or $Y_2O_3$, and at least one of $ZrO_2$ or $HfO_2$, based on the total weight of the glass;

e) $Al_2O_3$ and at least one of REO or $Y_2O_3$, wherein at least 60 percent by weight of the glass collectively comprises the $Al_2O_3$ and the at least one of REO or $Y_2O_3$, and wherein the glass contains not more than 20 percent by weight $SiO_2$ and not more than 20 percent by weight $B_2O_3$, based on the total weight of the glass;

f) $Al_2O_3$, at least one of REO or $Y_2O_3$, and at least one of $ZrO_2$ or $HfO_2$, wherein at least 60 percent by weight of the glass collectively comprises the $Al_2O_3$, at least one of REO or $Y_2O_3$, and at least one of $ZrO_2$ or $HfO_2$, and wherein the glass contains not more than 20 percent by weight $SiO_2$ and not more than 20 percent by weight $B_2O_3$, based on the total weight of the glass;

g) $Al_2O_3$ and at least one of REO or $Y_2O_3$, wherein at least 60 percent by weight of the glass comprise the $Al_2O_3$ and the at least one of REO or $Y_2O_3$, and wherein the glass contains not more than 40 percent by weight collectively $SiO_2$, $B_2O_3$, and $P_2O_5$, based on the total weight of the glass; or h) $Al_2O_3$, at least one of REO or $Y_2O_3$, and at least one of $ZrO_2$ or $HfO_2$, wherein at least 60 percent by weight of the glass collectively comprises the $Al_2O_3$, at least one of REO or $Y_2O_3$, and at least one of $ZrO_2$ or $HfO_2$, and wherein the glass contains not more than 40 percent by weight collectively $SiO_2$, $B_2O_3$, and $P_2O_5$, based on the total weight of the glass.

In another embodiment, the invention provides a method of making a dental article or an orthodontic appliance comprising the steps of:

combining a glass or glass-ceramic with a hardenable resin to form a mixture;

forming the dental article or the orthodontic appliance into a shape; hardening said mixture to form the dental article or orthodontic appliance, wherein said glass or glass-ceramic comprises at least one of:

a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;

b) at least 35 percent by weight $Al_2O_3$, based on the total weight of the glass or glass-ceramic, and a first metal oxide other than $Al_2O_3$, wherein the $Al_2O_3$ and the first metal oxide collectively comprise at least 70 percent by weight of the glass or glass-ceramic;

c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;

d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;

e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;

f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;

g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;

h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or i) a glass-ceramic having an average hardness of at least 13 GPa.

In another embodiment, the invention provides a method of making a dental article or orthodontic appliance comprising the steps of:

plasma or thermally spraying particles comprising metal oxide sources onto a suitable substrate such that the particles coalesce to form a shaped article; and optionally separating the shaped article or appliance from the substrate, wherein the shaped article comprises at least one of:

a) at least 35 percent by weight $Al_2O_3$, based on the total weight of the glass, and a first metal oxide other than $Al_2O_3$, wherein the glass contains not more than 10 percent by weight collectively $B_2O_3$, $GeO_2$, $P_2O_5$, $SiO_2$, $TeO_2$, and $V_2O_5$, based on the total weight of the glass;

b) at least 35 percent by weight $Al_2O_3$, based on the total weight of the glass, and a first metal oxide other than $Al_2O_3$, wherein the $Al_2O_3$ and the first metal oxide collectively comprise at least 70 percent by weight of the glass;

c) $Al_2O_3$ and at least one of REO or $Y_2O_3$, wherein at least 80 percent by weight of the glass collectively comprises the $Al_2O_3$ and the at least one of REO or $Y_2O_3$, based on the total weight of the glass;

d) $Al_2O_3$, at least one of REO or $Y_2O_3$, and at least one of $ZrO_2$ or $HfO_2$, wherein at least 80 percent by weight of the glass collectively comprises the $Al_2O_3$, at least one of REO or $Y_2O_3$, and at least one of $ZrO_2$ or $HfO_2$, based on the total weight of the glass;

e) $Al_2O_3$ and at least one of REO or $Y_2O_3$, wherein at least 60 percent by weight of the glass collectively comprises the $Al_2O_3$ and the at least one of REO or $Y_2O_3$, and wherein the glass contains not more than 20 percent by weight $SiO_2$ and not more than 20 percent by weight $B_2O_3$, based on the total weight of the glass;

f) $Al_2O_3$, at least one of REO or $Y_2O_3$, and at least one of $ZrO_2$ or $HfO_2$, wherein at least 60 percent by weight of the glass collectively comprises the $Al_2O_3$, at least one of REO or $Y_2O_3$, and at least one of $ZrO_2$ or $HfO_2$, and wherein the glass contains not more than 20 percent by weight $SiO_2$ and not more than 20 percent by weight $B_2O_3$, based on the total weight of the glass;

g) $Al_2O_3$ and at least one of REO or $Y_2O_3$, wherein at least 60 percent by weight of the glass comprise the $Al_2O_3$ and the at least one of REO or $Y_2O_3$, and wherein the glass contains not more than 40 percent by weight collectively $SiO_2$, $B_2O_3$, and $P_2O_5$, based on the total weight of the glass; or h) $Al_2O_3$, at least one of REO or $Y_2O_3$, and at least one of $ZrO_2$ or $HfO_2$, wherein at least 60 percent by weight of the glass collectively comprises the $Al_2O_3$, at least one of REO or $Y_2O_3$, and at least one of $ZrO_2$ or $HfO_2$, and wherein the glass contains not more than 40 percent by weight collectively $SiO_2$, $B_2O_3$, and $P_2O_5$, based on the total weight of the glass.

In another embodiment, the invention provides a kit comprising a plurality of dental or orthodontic components wherein at least one of the components includes a dental material, dental article, or orthodontic appliance comprising at least one of a glass or glass-ceramic described herein.

In another embodiment, the invention provides a method of performing a dental restoration comprising the steps of: preparing a dental site to be restored; and applying a restorative material comprising at least one of a ceramic, glass, or glass-ceramic described herein.

BRIEF DESCRIPTION OF THE FIGURES

FIG. 2a is a digital image of a scanning electron microscope (SEM) photomicrograph of a polished section of Example 1 material heat-treated at 1300° C.

FIG. 2b is a digital image of a scanning electron microscope (SEM) photomicrograph of a polished section of Example 1 material heat-treated at 1400° C.

DETAILED DESCRIPTION

Figure 1:
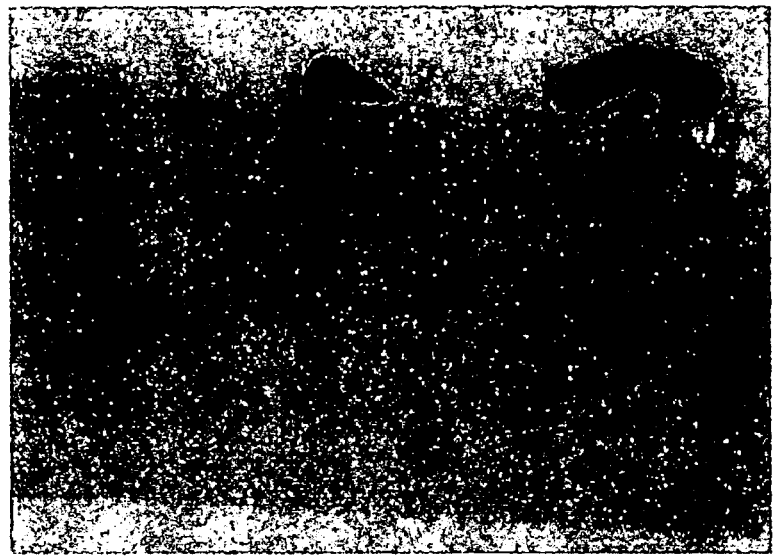
FIG. 1 is a digital image of an optical photomicrograph of a hot-pressed ceramic.

In this application:

"amorphous material" refers to material derived from a melt and/or a vapor phase that lacks any long range crystal structure as determined by x-ray diffraction and/or has an exothermic peak corresponding to the crystallization of the amorphous material as determined by a DTA (differential thermal analysis) as determined by the test described herein entitled "Differential Thermal Analysis";

"ceramic" includes amorphous material, glass, crystalline ceramic, glass-ceramic, and combinations thereof;

"complex metal oxide" refers to a metal oxide comprising two or more different metal elements and oxygen (e.g., $CeAl_{11}O_{18}$, $Dy_3Al_5O_{12}$, $MgAl_2O_4$, and $Y_3Al_5O_{12}$);

"complex $Al_2O_3$.metal oxide" refers to a complex metal oxide comprising, on a theoretical oxide basis, $Al_2O_3$ and one or more metal elements other than Al (e.g., $CeAl_{11}O_{18}$, $Dy_3Al_5O_{12}$, $MgAl_2O_4$, and $Y_3Al_5O_{12}$);

"complex $Al_2O_3.Y_2O_3$" refers to a complex metal oxide comprising, on a theoretical oxide basis, $Al_2O_3$ and $Y_2O_3$ (e.g., $Y_3Al_5O_{12}$);

"complex $Al_2O_3$.REO" refers to a complex metal oxide comprising, on a theoretical oxide basis, $Al_2O_3$ and rare earth oxide (e.g., $CeAl_{11}O_{18}$ and $Dy_3Al_5O_{12}$);

"dental article" refers to a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, and bridge frameworks;

"dental material" refers to a dental composition such as a paste which when hardens forms a dental article;

"glass" refers to amorphous material exhibiting a glass transition temperature;

"glass-ceramic" refers to ceramics comprising crystals formed by heat-treating amorphous material;

"hardenable" refers to a material that can be cured or solidified (e.g., by heating to remove solvent, heating to cause polymerization, chemical crosslinking, radiation-induced polymerization or crosslinking, or the like);

"hardened" refers to material that is cured or solidified (e.g., by heating to remove solvent, heating to cause polymerization, chemical crosslinking, radiation-induced polymerization or crosslinking, or the like);

"hardening" refers to a method of curing or solidifying (e.g., by heating to remove solvent, heating to cause polymerization, chemical crosslinking, radiation-induced polymerization or crosslinking, or the like);

"orthodontic appliance" refers to any device intended for mounting on a tooth, and used to transmit to the tooth corrective force from an arch wire, spring, elastic, or other force-applying component. Examples include brackets, buccal tubes, cleats, and buttons;

"prosthesis" includes crowns, bridges, inlays, onlays, veneers, copings, frameworks, and abutments;

"restoratives" includes veneers, crowns, inlays, onlays, and bridge structures;

"$T_g$" refers to the glass transition temperature as determined by the test described herein entitled "Differential Thermal Analysis";

"$T_x$" refers to the crystallization temperature as determined by the test described herein entitled "Differential Thermal Analysis";

"rare earth oxides" refers to cerium oxide (e.g., $CeO_2$), dysprosium oxide (e.g., $Dy_2O_3$), erbium oxide (e.g., $Er_2O_3$), europium oxide (e.g., $Eu_2O_3$), gadolinium (e.g., $Gd_2O_3$), holmium oxide (e.g., $Ho_2O_3$), lanthanum oxide (e.g., $La_2O_3$), lutetium oxide (e.g., $Lu_2O_3$), neodymium oxide (e.g., $Nd_2O_3$), praseodymium oxide (e.g., $Pr_6O_{11}$), samarium oxide (e.g., $Sm_2O_3$), terbium (e.g., $Tb_2O_3$), thorium oxide (e.g., $Th_4O_7$), thulium (e.g., $Tm_2O_3$), and ytterbium oxide (e.g., $Yb_2O_3$), and combinations thereof; and "REO" refers to rare earth oxide(s).

Further, it is understood herein that unless it is stated that a metal oxide (e.g., $Al_2O_3$, complex $Al_2O_3$.metal oxide, etc.) is crystalline, for example, in a glass-ceramic, it may be amorphous, crystalline, or portions amorphous, and portions crystalline. For example, if a glass-ceramic comprises $Al_2O_3$ and $ZrO_2$, the $Al_2O_3$ and $ZrO_2$ may each be in an amorphous state, crystalline state, or portions in an amorphous state and portions in a crystalline state, or even as a reaction product with another metal oxide(s) (e.g., unless it is stated that, for example, $Al_2O_3$ is present as crystalline $Al_2O_3$ or a specific crystalline phase of $Al_2O_3$ (e.g., alpha $Al_2O_3$), it may be present as crystalline $Al_2O_3$ and/or as part of one or more crystalline complex $Al_2O_3$.metal oxides).

Further, it is understood that glass-ceramics formed by heating amorphous material not exhibiting a $T_g$ may not actually comprise glass, but rather may comprise the crystals and amorphous material that does not exhibiting a $T_g$.

Some advantages of using the ceramics, glasses, and glass-ceramics described herein for dental and orthodontic applications include improved processing abilities of complex-shaped articles combined with excellent material properties that are akin to those of structural ceramics (e.g., $Al_2O_3$ and $ZrO_2$). These useful dental shapes can be generated by either glass-like viscous flow or by machining blanks in amorphous or partially crystalline states.

Ceramics, Glass, and Glass-Ceramics

In some embodiments according to the present invention, the ceramic, the glass and the glass-ceramic comprises at least 35 (in some embodiments, at least 40, 45, 50, 55, 60, 65, 70, or even at least 75) percent by weight $Al_2O_3$, based on the total weight of the ceramic, glass, or glass-ceramic, respectively, and a first metal oxide other than $Al_2O_3$ (e.g., $Y_2O_3$, REO, MgO, $TiO_2$, $Cr_2O_3$, CuO, NiO, and $Fe_2O_3$), and optionally a second, (third, etc.) different metal oxide other than $Al_2O_3$ (e.g., $Y_2O_3$, REO, MgO, $TiO_2$, $Cr_2O_3$, CuO, NiO, and, $Fe_2O_3$), wherein the glass or glass-ceramic, respectively, contains not more than 10 (in some embodiments, not more than 5, 4, 3, 2, 1, or zero) percent by weight collectively $B_2O_3$, $GeO_2$, $P_2O_5$, $SiO_2$, $TeO_2$, and $V_2O_5$, based on the total weight of the glass or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the glass and the glass-ceramic comprises at least 35 (in some embodiments, at least 40, 45, 50, 55, 60, 65, 70, or even at least 75) percent by weight $Al_2O_3$, based on the total weight of the ceramic, glass, or glass-ceramic, respectively, and a first metal oxide other than $Al_2O_3$ (e.g., $Y_2O_3$, REO, MgO, $TiO_2$, $Cr_2O_3$, CuO, NiO, and $Fe_2O_3$), and optionally, a second, (third etc.) different metal oxide other than $Al_2O_3$ (e.g., $Y_2O_3$, REO, MgO, $TiO_2$, $Cr_2O_3$, CuO, NiO, and, $Fe_2O_3$), wherein the $Al_2O_3$, first metal oxide, and second metal oxide collectively comprise at least 80 (in some embodiments, at least 85, 90, 95, or 100) percent by weight of the ceramic, glass, or glass-ceramic, respectively, and wherein the ceramic, glass, or glass-ceramic contains not more than 20 (in some embodiments, not more than 15, 10, 5, 4, 3, 2, 1, or even zero) percent by weight collectively $B_2O_3$, $GeO_2$, $P_2O_5$, $SiO_2$, $TeO_2$, and $V_2O_5$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the ceramic, the glass, and the glass-ceramic comprises $Al_2O_3$ and at least one of REO or $Y_2O_3$, wherein at least 80 (in some embodiments, at least 85, 90, 95, or even 100) percent by weight of the ceramic, glass, or glass-ceramic, respectively, collectively comprises the $Al_2O_3$ and the at least one of REO or $Y_2O_3$, based on the total weight of the ceramic, glass, or glass-ceramic, respectively.

In some embodiments according to the present invention, the ceramic, the glass, and the glass-ceramic comprises $Al_2O_3$, at least one of REO or $Y_2O_3$, and at least one of $ZrO_2$ or $HfO_2$, wherein at least 80 (in some embodiments, at least 85, 90, 95, or even 100) percent by weight of the ceramic, glass, or glass-ceramic, respectively, collectively comprises the $Al_2O_3$, at least one of REO or $Y_2O_3$, and at least one of $ZrO_2$ or $HfO_2$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the ceramic, the glass, and the glass-ceramic comprises $Al_2O_3$ and at least one of REO or $Y_2O_3$, wherein at least 60 (in some embodiments, 65, 70, 75, 80, 85, 90, 95, or even at least 100) percent by weight of the ceramic, glass, or glass-ceramic, respectively, collectively comprises the $Al_2O_3$ and the at least one of REO or $Y_2O_3$, and wherein the ceramic, glass, or glass-ceramic, respectively, contains not more than 20 (in some embodiments, not more than 15, 10, 5, or even zero) percent by weight $SiO_2$ and not more than 20 (in some embodiments, not more than 15, 10, 5, or even zero) percent by weight $B_2O_3$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the ceramic, the glass, and the glass-ceramic comprises $Al_2O_3$, at least one of REO or $Y_2O_3$, and at least one of $ZrO_2$ or $HfO_2$, wherein at least 60 (in some embodiments, 65, 70, 75, 80, 85, 90, 95, or even at least 100) percent by weight of the ceramic, glass, or glass-ceramic, respectively, collectively comprises the $Al_2O_3$, at least one of REO or $Y_2O_3$, and at least one of $ZrO_2$ or $HfO_2$, and wherein the ceramic, glass, or glass-ceramic, respectively, contains not more than 20 (in some embodiments, less than 15, 10, 5, or even zero) percent by weight $SiO_2$ and not more than 20 (in some embodiments, not more than 15, 10, 5, or even zero) percent by weight $B_2O_3$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the ceramic, the glass, and the glass-ceramic comprises $Al_2O_3$ and at least one of REO or $Y_2O_3$, wherein at least 60 (in some embodiments, 65, 70, 75, 80, 85, 90, 95, or even at least 100) percent by weight of the ceramic, glass, or glass-ceramic, respectively, comprise the $Al_2O_3$ and the at least one of REO or $Y_2O_3$, and wherein the ceramic, glass, or glass-ceramic, respectively, contains not more than 40 (in some embodiments, not more than 35, 30, 25, 20, 15, 10, 5, or even zero) percent by weight collectively $SiO_2$, $B_2O_3$, and $P_2O_5$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

In some embodiments according to the present invention, the ceramic, the glass, and the glass-ceramic comprises $Al_2O_3$, at least one of REO or $Y_2O_3$, and at least one of $ZrO_2$ or $HfO_2$, wherein at least 60 (in some embodiments, 65, 70, 75, 80, 85, 90, 95, or even at least 100) percent by weight of the ceramic, glass, or glass-ceramic, respectively, collectively comprises the $Al_2O_3$, at least one of REO or $Y_2O_3$, and at least one of $ZrO_2$ or $HfO_2$, and wherein the ceramic, glass, or glass-ceramic, respectively, contains not more than 40 (in some embodiments, not more than 35, 30, 25, 20, 15, 10, 5, or even zero) percent by weight collectively $SiO_2$, $B_2O_3$, and $P_2O_5$, based on the total weight of the ceramic, glass, or glass-ceramic, respectively. Embodiments of the glass-ceramic have an average hardness of at least 13 GPa, 14 GPa, 15 GPa, 16 GPa, 17 GPa, 18 GPa, or even at least 19 GPa.

Some embodiments of glass-ceramics according to the present invention may comprise, for example, at least 1, 2, 3, 5, 10, 15, 20, 25, 30, 35, 40, 45, 50, 55, 60, 65, 70, 75, 80, 85, 90, 95, or even 100 percent by volume glass. Some embodiments of glass-ceramics according to the present invention may comprise, for example, at least 1, 2, 3, 5, 10, 15, 20, 25, 30, 35, 40, 45, 50, 55, 60, 65, 70, 75, 80, 85, 90, 95, 97, 98, 99, or even 100 percent by volume crystalline ceramic, based on the total volume of the glass-ceramic.

Some amorphous materials used to make glasses and the glass-ceramics made therefrom, comprise 20 to at least 70 percent by weight (in some embodiments, 30 to at least 70 percent, 40 to at least 70 percent, 50 to at least 70 percent, or even 60 to at least 70 percent) $Al_2O_3$; 0 to 70 percent by weight (in some embodiments, 0 to 25 percent, or even 0 to 10 percent) $Y_2O_3$; and 0 to 70 percent by weight (in some embodiments, 0 to 50 percent, 0 to 25 percent, or even 0 to 10 percent) at least one of $ZrO_2$ or $HfO_2$, based on the total weight of the amorphous material or glass-ceramic. In some embodiments, such amorphous materials, and the glass-ceramics made therefrom, comprise at least 30 percent by weight, at least 40 percent by weight, at least 50 percent by weight, at least 60 percent by weight, or even at least 70 percent by weight $Al_2O_3$, based on the total weight of the amorphous material or glass-ceramic. In some embodiments, such amorphous materials, and the glass-ceramics made therefrom, contain less than 40 (in some embodiments, less than 35, 30, 25, 20, 15, 10, 5, 4, 3, 2, 1, or even zero) percent by weight collectively $SiO_2$, $B_2O_3$, and $P_2O_5$, based on the total weight of the amorphous material or glass-ceramic. In some embodiments, such amorphous materials, and the glass-ceramics made therefrom, contain less than 20 (in some embodiments, less than 15, 10, 5, or even zero) percent by weight $SiO_2$ and less than 20 (preferably, less than 15, 10, 5, or even zero) percent by weight $B_2O_3$, based on the total weight of the amorphous material or glass-ceramic.

Some amorphous materials used to make glasses and the glass-ceramics made therefrom, comprise 20 to at least 70 percent by weight (in some embodiments, 30 to at least 70 percent, 40 to at least 70 percent, 50 to at least 70 percent, or even 60 to at least 70 percent) $Al_2O_3$; 0 to 70 percent by weight (in some embodiments, 0 to 50 percent, 0 to 25 percent, or even 0 to 10 percent) REO; 0 to 50 percent by weight (in some embodiments, 0 to 25 percent, or even 0 to 10 percent) at least one of $ZrO_2$ or $HfO_2$, based on the total weight of the amorphous material or glass-ceramic. In some embodiments, such amorphous materials, and the glass-ceramics made therefrom, comprise 30 percent by weight, at least 40 percent by weight, at least 50 percent by weight, at least 60 percent by weight, or even at least 70 percent by weight $Al_2O_3$, based on the total weight of the amorphous material or glass-ceramic. In some embodiments, such amorphous materials, and the glass-ceramics made therefrom, comprise less than 40 (in some embodiments, less than 35, 30, 25, 20, 15, 10, 5, 4, 3, 2, 1, or even zero) percent by weight collectively $SiO_2$, $B_2O_3$, and $P_2O_5$, based on the total weight of the amorphous materials or glass-ceramic. In some embodiments, such glasses, and the glass-ceramics made therefrom, contain less than 20 (in some embodiments, less than 15, 10, 5, or even zero) percent by weight $SiO_2$ and less than 20 (in some embodiments, less than 15, 10, 5, or even zero) percent by weight $B_2O_3$, based on the total weight of the amorphous material or glass-ceramic.

Some amorphous materials used to make glasses and the glass-ceramics made therefrom, comprise 20 to at least 70 percent by weight (in some embodiments, 30 to at least 70 percent, 40 to at least 70 percent, 50 to at least 70 percent, or even 60 to 70 percent) $Al_2O_3$; 0 to 70 percent by weight (in some embodiments, 0 to 50 percent, 0 to 25 percent, or even 0 to 10 percent) $Y_2O_3$; 0 to 70 percent by weight (in some embodiments, 0 to 50 percent, 0 to 25 percent, or even 0 to 10 percent) REO; 0 to 50 percent by weight (in some embodiments, 0 to 25 percent, or even 0 to 10 percent) at least one of $ZrO_2$ or $HfO_2$, based on the total weight of the amorphous material or glass-ceramic. In some embodiments, such amorphous materials, and the glass-ceramics made therefrom, comprise at least 30 percent by weight, at least 40 percent by weight, at least 50 percent by weight, at least 60 percent by weight, or even at least 70 percent by weight $Al_2O_3$, based on the total weight of the amorphous material or glass-ceramic. In some embodiments, such amorphous materials, and the glass-ceramics made therefrom, contain less than 40 (in some embodiments, less than 35, 30, 25, 20, 15, 10, 5, 4, 3, 2, 1, or even zero) percent by weight collectively $SiO_2$, $B_2O_3$, and $P_2O_5$, based on the total weight of the amorphous material or glass-ceramic. In some embodiments, such amorphous materials, and the glass-ceramics made therefrom, contain less than 20 (in some embodiments, less than 15, 10, 5, or even zero) percent by weight $SiO_2$ and less than 20 (in some embodiments, less than 15, 10, 5, or even zero) percent by weight $B_2O_3$, based on the total weight of the amorphous material or glass-ceramic.

Amorphous materials (e.g., glasses), ceramics comprising the amorphous material, particles comprising the amorphous material, etc. can be made, for example, by heating (including in a flame) the appropriate metal oxide sources to form a melt, desirably a homogenous melt, and then rapidly cooling the melt to provide amorphous material. The metal oxide sources and other additives can be in any form suitable to the process and equipment used to make the glass or glass-ceramics. Desirable cooling rates include those of 10 K/s and greater. Embodiments of amorphous materials can be made, for example, by melting the metal oxide sources in any suitable furnace (e.g., an inductive heated furnace, a gas-fired furnace, or an electrical furnace), or, for example, in a plasma. The resulting melt is cooled (e.g., discharging the melt into a cooling media (e.g., high velocity air jets, liquids, metal plates (including chilled metal plates), metal rolls (including chilled metal rolls), metal balls (including chilled metal balls), and the like)).

Further, other techniques for making melts and glasses, and otherwise forming amorphous material include vapor phase quenching, melt-extraction, plasma spraying, and gas or centrifugal atomization. For additional details regarding plasma spraying, see, for example, U.S. Publication No. 2004-0023078 A1, the disclosure of which is incorporated herein by reference.

Gas atomization involves melting feed particles to convert them to melt. A thin stream of such melt is atomized through contact with a disruptive air jet (i.e., the stream is divided into fine droplets). The resulting substantially discrete, generally ellipsoidal amorphous material comprising particles (e.g., beads) are then recovered. Examples of bead sizes include those having a diameter in a range of about 5 micrometers to about 3 mm. Melt-extraction can be carried out, for example, as disclosed in U.S. Pat. No. 5,605,870, the disclosure of which is incorporated herein by reference. Containerless glass forming techniques utilizing laser beam heating as disclosed, for example, in U.S. Pat. No. 6,482,758, the disclosure of which is incorporated herein by reference, may also be useful in making glass, glass-ceramics and amorphous materials.

Embodiments of amorphous material can be made utilizing flame fusion as disclosed, for example, in U.S. Pat. No. 6,254,981, the disclosure of which is incorporated herein by reference. In this method, the metal oxide sources materials are fed (e.g., in the form of particles, sometimes referred to as "feed particles") directly into a burner (e.g., a methane-air burner, an acetylene-oxygen burner, a hydrogen-oxygen burner, and like), and then quenched, for example, in water, cooling oil, air, or the like. Feed particles can be formed, for example, by grinding, agglomerating (e.g., spray-drying), melting, or sintering the metal oxide sources. The size of feed particles fed into the flame generally determine the size of the resulting amorphous material comprising particles.

Embodiments of amorphous materials can also be obtained by other techniques, such as: laser spin melt with free fall cooling, Taylor wire technique, plasmatron technique, hammer and anvil technique, centrifugal quenching, air gun splat cooling, single roller and twin roller quenching, roller-plate quenching and pendant drop melt extraction (see, e.g., *Rapid Solidification of Ceramics*, Brockway et. al, Metals And Ceramics Information Center, A Department of Defense Information Analysis Center, Columbus, Ohio, January, 1984, the disclosure of which is incorporated here as a reference). Embodiments of amorphous materials may also be obtained by other techniques, such as: thermal (including flame or laser or plasma-assisted) pyrolysis of suitable precursors, physical vapor synthesis (PVS) of metal precursors and mechanochemical processing.

The cooling rate is believed to affect the properties of the quenched amorphous material. For instance, glass transition temperature, density, and other properties of glass typically change with cooling rates.

Rapid cooling may also be conducted under controlled atmospheres, such as a reducing, neutral, or oxidizing environment to maintain and/or influence the desired oxidation states, etc. during cooling. The atmosphere can also influence amorphous material formation by influencing crystallization kinetics from undercooled liquid. For example, larger undercooling of $Al_2O_3$ melts without crystallization has been reported in argon atmosphere as compared to that in air.

Amorphous materials can also be made by a sol-gel process. The sol-gel process comprises the steps of forming a precursor composition in the form of a dispersion, sol, or solution in an aqueous or organic liquid medium. The precursor composition can be processed into a variety of useful forms including coatings, films, powders, gels, aerogels, dense bulk shapes, fibers, flakes, granules, and nanoclusters. Further details of these processes can be found in *Sol-Gel Science* by C. Jeffrey Brinker and George W. Scherer (Academic Press, 1990), the disclosure of which is incorporated herein by reference. Further details about the synthesis of nanoclusters can be found in PCT Publication No. WO 0130306(A1), the disclosure of which is incorporated herein by reference. Another method of making powders is by the spray pyrolysis of a precursor containing one or more glycolato polymetallooxanes dissolved in a volatile organic solvent; details about this process can be found in U.S. Pat. No. 5,958,361, the disclosure of which is incorporated herein by reference.

Useful amorphous material formulations include those at or near a eutectic composition(s) (e.g., binary and ternary eutectic compositions). In addition to compositions disclosed herein, other compositions, including quaternary and other higher order eutectic compositions, may be apparent to those skilled in the art after reviewing the present disclosure.

Sources, including commercial sources, of (on a theoretical oxide basis) $Al_2O_3$ include bauxite (including both natural occurring bauxite and synthetically produced bauxite), calcined bauxite, hydrated aluminas (e.g., boehmite and gibbsite), aluminum, Bayer process alumina, aluminum ore, gamma alumina, alpha alumina, aluminum salts, aluminum nitrates, and combinations thereof. The $Al_2O_3$ source may contain, or only provide, $Al_2O_3$. Alternatively, the $Al_2O_3$ source may contain, or provide $Al_2O_3$, as well as one or more metal oxides other than $Al_2O_3$ (including materials of or containing complex $Al_2O_3$ metal oxides (e.g., $Dy_3Al_5O_{12}$, $Y_3Al_5O_{12}$, $CeAl_{11}O_{18}$, etc.)).

Sources, including commercial sources, of rare earth oxides include rare earth oxide powders, rare earth metals, rare earth-containing ores (e.g., bastnasite and monazite), rare earth salts, rare earth nitrates, and rare earth carbonates. The rare earth oxide(s) source may contain, or only provide, rare earth oxide(s). Alternatively, the rare earth oxide(s) source may contain, or provide rare earth oxide(s), as well as one or more metal oxides other than rare earth oxide(s) (including materials of or containing complex rare earth oxides or other metal oxides (e.g., $Dy_3Al_5O_{12}$, $CeAl_{11}O_{18}$, etc.)).

Sources, including commercial sources, of (on a theoretical oxide basis) $Y_2O_3$ include yttrium oxide powders, yttrium, yttrium-containing ores, and yttrium salts (e.g., yttrium carbonates, nitrates, chlorides, hydroxides, and combinations thereof). The $Y_2O_3$ source may contain, or only provide, $Y_2O_3$. Alternatively, the $Y_2O_3$ source may contain, or provide $Y_2O_3$, as well as one or more metal oxides other than $Y_2O_3$ (including materials of or containing complex $Y_2O_3$.metal oxides (e.g., $Y_3Al_5O_{12}$)).

Sources, including commercial sources, of (on a theoretical oxide basis) $ZrO_2$ include zirconium oxide powders, zircon sand, zirconium, zirconium-containing ores, and zirconium salts (e.g., zirconium carbonates, acetates, nitrates, chlorides, hydroxides, and combinations thereof). In addition, or alternatively, the $ZrO_2$ source may contain, or provide $ZrO_2$, as well as other metal oxides such as hafnia. Sources, including commercial sources, of (on a theoretical oxide basis) $HfO_2$ include hafnium oxide powders, hafnium, hafnium-containing ores, and hafnium salts. In addition, or alternatively, the $HfO_2$ source may contain, or provide $HfO_2$, as well as other metal oxides such as $ZrO_2$.

Other useful metal oxide may also include, on a theoretical oxide basis, BaO, CaO, $Cr_2O_3$, CoO, $Fe_2O_3$, $GeO_2$, $Li_2O$, MgO, MnO, NiO, $Na_2O$, $Sc_2O_3$, SrO, $TiO_2$, ZnO, and combinations thereof. Sources, including commercial sources, include the oxides themselves, complex oxides, ores, carbonates, acetates, nitrates, chlorides, hydroxides, etc. These metal oxides are added to modify a physical property of the resulting particles and/or improve processing. These metal oxides are typically added anywhere from 0 to 50 percent by weight, in some embodiments preferably 0 to 25 percent by weight and more preferably 0 to 50 percent by weight of the glass-ceramic depending, for example, upon the desired property.

The particular selection of metal oxide sources and other additives for making ceramics typically takes into account, for example, the desired composition and microstructure of the resulting ceramics, the desired degree of crystallinity, if any, the desired physical properties (e.g., hardness or toughness) of the resulting ceramics, avoiding or minimizing the presence of undesirable impurities, the desired characteristics of the resulting ceramics, and/or the particular process (including equipment and any purification of the raw materials before and/or during fusion and/or solidification) being used to prepare the ceramics.

In some instances, it may be preferred to incorporate limited amounts of metal oxides selected from the group consisting of: $Na_2O$, $P_2O_5$, $SiO_2$, $TeO_2$, $V_2O_5$, and combinations thereof. Sources, including commercial sources, include the oxides themselves, complex oxides, ores, carbonates, acetates, nitrates, chlorides, hydroxides, etc. These metal oxides may be added, for example, to modify a physical property of the resulting particles and/or improve processing. These metal oxides when used are typically added from greater than 0 to 20 percent by weight, preferably greater than 0 to 5 percent by weight and more preferably greater than 0 to 2 percent by weight of the glass-ceramic depending, for example, upon the desired property.

The addition of certain metal oxides may alter the properties and/or crystalline structure or microstructure of a glass-ceramic, as well as the processing of the raw materials and intermediates in making the glass-ceramic. For example, oxide additions such as MgO, CaO, $Li_2O$, and $Na_2O$ have been observed to alter both the $T_g$ (for a glass) and $T_x$ (wherein $T_x$ is the crystallization temperature) of amorphous material. Although not wishing to be bound by theory, it is believed that such additions influence glass formation. Further, for example, such oxide additions may decrease the melting temperature of the overall system (i.e., drive the system toward lower melting eutectic), and ease of amorphous material-formation. Complex eutectics in multi-component systems (quaternary, etc.) may result in better amorphous material-forming ability. The viscosity of the liquid melt and viscosity of the glass in its "working" range may also be affected by the addition of certain metal oxides such as MgO, CaO, $Li_2O$, and $Na_2O$. It is also within the scope of the present invention to incorporate at least one of halogens (e.g., fluorine and chlorine), or chalcogenides (e.g., sulfides, selenides, and tellurides) into the amorphous materials, and the glass-ceramics made therefrom.

Crystallization of the amorphous material and ceramic comprising the amorphous material may also be affected by the additions of certain materials. For example, certain metals, metal oxides (e.g., titanates and zirconates), and fluorides, for example, may act as nucleation agents resulting in beneficial heterogeneous nucleation of crystals. Also, addition of some oxides may change nature of metastable phases devitrifying from the amorphous material upon reheating. In another aspect, for ceramics comprising crystalline $ZrO_2$, it may be desirable to add metal oxides (e.g., $Y_2O_3$, $TiO_2$, CaO, and MgO) that are known to stabilize tetragonal/cubic form of $ZrO_2$.

The microstructure or phase composition (glassy/amorphous/crystalline) of a material can be determined in a number of ways. Various information can be obtained using optical microscopy, electron microscopy, differential thermal analysis (DTA), and x-ray diffraction (XRD), for example.

Using optical microscopy, amorphous material is typically predominantly transparent due to the lack of light scattering centers such as crystal boundaries, while crystalline material shows a crystalline structure and is opaque due to light scattering effects.

Using DTA, the material is classified as amorphous if the corresponding DTA trace of the material contains an exothermic crystallization event ($T_x$). If the same trace also contains an endothermic event ($T_g$) at a temperature lower than $T_x$, it is considered to consist of a glass phase. If the DTA trace of the material contains no such events, it is considered to contain crystalline phases.

Differential thermal analysis (DTA) can be conducted using the following method. DTA runs can be made (using an instrument such as that obtained from Netzsch Instruments, Selb, Germany, under the trade designation "NETZSCH STA 409 DTA/TGA") using a −140+170 mesh size fraction (i.e., the fraction collected between 105-micrometer opening size and 90-micrometer opening size screens). An amount of each screened sample (typically about 400 milligrams (mg)) is placed in a 100-microliter $Al_2O_3$ sample holder. Each sample is heated in static air at a rate of 10° C./minute from room temperature (about 25° C.) to 1100° C.

Using powder x-ray diffraction, XRD, (using an x-ray diffractometer such as that obtained under the trade designation "PHILLIPS XRG 3100" from Phillips, Mahwah, N.J., with copper $K_{\alpha 1}$ radiation of 1.54050 Angstrom) the phases present in a material can be determined by comparing the peaks present in the XRD trace of the crystallized material to XRD patterns of crystalline phases provided in JCPDS (Joint Committee on Powder Diffraction Standards) databases, published by International Center for Diffraction Data. Furthermore, an XRD can be used qualitatively to determine types of phases. The presence of a broad diffused intensity peak is taken as an indication of the amorphous nature of a material. The existence of both a broad peak and well-defined peaks is taken as an indication of existence of crystalline matter within an amorphous matrix.

The initially formed amorphous material or ceramic (including glass prior to crystallization) may be larger in size than that desired. The amorphous material or ceramic can be converted into smaller pieces using crushing and/or comminuting techniques known in the art, including roll crushing, canary milling, jaw crushing, hammer milling, ball milling, jet milling, impact crushing, and the like. The shape of the ceramic (including glass prior to crystallization) may depend, for example, on the composition and/or microstructure of the ceramic, the geometry in which it was cooled, and the manner in which the ceramic is crushed (i.e., the crushing technique used). In general, where a "blocky" shape is preferred, more energy may be employed to achieve this shape. Conversely, where a "sharp" shape is preferred, less energy may be employed to achieve this shape. The crushing technique may also be changed to achieve different desired shapes. The resulting particles may have an average aspect ratio ranging from 1:1 to 5:1, typically 1.25:1 to 3:1, and preferably 1.5:1 to 2.5:1.

It is also within the scope of the present invention, for example, to directly form ceramic (including glass prior to crystallization) in desired shapes. For example, ceramic (including glass prior to crystallization) may be formed (including molded) by pouring or forming the melt into a mold.

It is also within the scope of the present invention, for example, to fabricate the ceramic (including glass prior to crystallization) by coalescing. This coalescing step in essence forms a larger sized body from two or more smaller particles. For example, amorphous material comprising particles (obtained, for example, by crushing) (including beads and microspheres), fibers, etc. may be formed into an article. For example, ceramic (including glass prior to crystallization), may also be provided by heating, for example, particles comprising the amorphous material, and/or fibers, etc. above the $T_g$ such that the particles, etc. coalesce to form a shape and cooling the coalesced shape. The temperature and pressure used for coalescing may depend, for example, upon composition of the amorphous material and the desired density of the resulting material. The temperature should be desirably below glass crystallization temperature, and for glasses, greater than the glass transition temperature. In some embodiments, the temperature used in coalescing may exceed the glass crystallization temperature. In certain embodiments, the heating is conducted at a temperature in a range of about 850° C. to about 1100° C. (in some embodiments, preferably 900° C. to 1000° C.). Typically, the amorphous material is under pressure (e.g., greater than zero to 1 GPa or more) during coalescence to aid the coalescence of the amorphous material.

In one embodiment, a charge of the particles, etc. is placed into a die and hot-pressing is performed at temperatures above glass transition where viscous flow of glass leads to coalescence into a relatively large part. Examples of typical coalescing techniques include hot pressing, hot isostatic pressure, hot extrusion, and the like. During this coalescence step, articles of complex shapes can be obtained by choosing suitable die constructions. Typically, it is generally preferred to cool the resulting coalesced body before further heat treatment.

In another embodiment, a coalesced perform comprising glass is placed into a die and is molded into useful shapes under the action of heat and pressure such that the perform flows. The perform may be glassy or partially crystalline. The perform may have a range of densities of from 50 to 100 of theoretical densities.

It is also within the scope of the present invention to conduct additional heat-treatment to further improve desirable properties of the material. For example, hot-isostatic pressing may be conducted (e.g., at temperatures from about 900° C. to about 1400° C.) to remove residual porosity, increasing the density of the material. Optionally, the resulting, coalesced article can be heat-treated to provide a glass-ceramic, crystalline ceramic, or ceramic otherwise comprising crystalline ceramic.

Coalescence of the amorphous material and/or glass-ceramic (e.g., particles) may also be accomplished by a variety of methods, including pressureless or pressure sintering (e.g., sintering, plasma assisted sintering, hot pressing, HIPing, hot forging, hot extrusion, etc.). Coalescence of the amorphous material and/or glass-ceramic or shaping of an already coalesced body may be accomplished with the use of suitable dental presses that can deliver the required temperature and heat. One embodiment of this process comprises the steps of forming a refractory investment mold, inserting the material into the mold, heating, applying pressure to the material such that it fills the mold cavity to form the desired shape. An example of such a process is described in U.S. Pat. No. 6,465,106, incorporated by reference herein. A commercial example of such a press is the Intra-Tech ProPress 100 (Whip-Mix Inc., Farmington, Ky.).

In another embodiment, the materials of this invention can be formed into mill blanks and machined to a desired shaped product. The machining step can be accomplished in glassy, crystalline, or intermediate stages. Digitized CAD/CAM machining can be employed for this task. Examples of such systems include CEREC (Sirona Dental Systems GmbH, Bensheim, Germany) and Lava (3M Company, St. Paul, Minn.). It has been surprisingly found that despite the high-strength nature of the material, it is quite machinable.

Heat-treatment can be carried out in any of a variety of ways, including those known in the art for heat-treating glass to provide glass-ceramics. For example, heat-treatment can be conducted in batches, for example, using resistive, inductively, or gas heated furnaces. Alternatively, for example, heat-treatment can be conducted continuously, for example, using a rotary kiln, fluidized bed furnace, or pendulum kiln. In the case of a rotary kiln or pendulum kiln, the material is fed directly into a kiln operating at the elevated temperature. The time at the elevated temperature may range from a few seconds (in some embodiments even less than 5 seconds) to a few minutes to several hours. The temperature may range anywhere from the $T_x$ of the amorphous material to 1600° C., from 900° C. to 1600° C., or between 1200° C. to 1500° C.

The glass is heat-treated to at least partially crystallize the amorphous material to provide glass-ceramic. The heat-treatment of certain glasses to form glass-ceramics is well known in the art. The heating conditions are generally carefully controlled to nucleate and grow crystals to provide desired microstructure and properties. One skilled in the art can determine the appropriate conditions from a Time-Temperature-Transformation (TTT) study of the glass using techniques known in the art. One skilled in the art, after reading the disclosure of the present invention should be able to provide TTT curves for glasses, determine the appropriate nucleation and/or crystal growth conditions to provide glass-ceramics.

In some embodiments of the present invention, the glasses or ceramics comprising glass may be annealed prior to heat-treatment. In such cases, annealing is typically done at a temperature less than the $T_x$ of the glass for a time from a few seconds to a few hours or even days. Typically, the annealing is done for a period of less than 3 hours, or even less than an hour. Optionally, annealing may also be carried out in atmospheres other than air.

Heat-treatment may occur, for example, by feeding the material directly into a furnace at the elevated temperature. Alternatively, for example, the material may be fed into a furnace at a much lower temperature (e.g., room temperature) and then heated to desired temperature at a predetermined heating rate. It is within the scope of the present invention to conduct heat-treatment in an atmosphere other than air. In some cases it might be even desirable to heat-treat in a reducing atmosphere(s). Also, for example, it may be desirable to heat-treat under gas pressure as in, for example, hot-isostatic press, or in gas pressure furnace. Although not wanting to be bound by theory, it is believed that the $T_g$ and $T_x$, as well as the $T_x$–$T_g$ of glasses according to the present application may shift depending upon the atmospheres used during the heat treatment. It is also believed that the choice of atmospheres may affect oxidation states of some of the components of the glasses and glass-ceramics. Such variation in oxidation state can bring about varying coloration of glasses and glass-ceramics. In addition, nucleation and crystallization steps can be affected by atmospheres (e.g., the atmosphere may affect the atomic mobilities of some species of the glasses).

Typically, glass-ceramics are stronger than the amorphous materials from which they are formed. Hence, the strength of the material may be adjusted, for example, by the degree to which the amorphous material is converted to crystalline ceramic phase(s). Alternatively, or in addition, the strength of the material may also be affected, for example, by the number of nucleation sites created, which may in turn be used to affect the number, and in turn the size of the crystals of the crystalline phase(s). For additional details regarding forming glass-ceramics, see, for example *Glass-Ceramics*, P. W. McMillan, Academic Press, Inc., 2nd edition, 1979, the disclosure of which is incorporated herein by reference.

As compared to many other types of ceramic processing (e.g., sintering of a calcined material to a dense, sintered ceramic material), there is relatively little shrinkage (typically, less than 30 percent by volume; in some embodiments, less than 20 percent, 10 percent, 5 percent, or even less than 3 percent by volume) during crystallization of the glass to form the glass-ceramic. The actual amount of shrinkage depends, for example, on the composition of the glass, the heat-treatment time, the heat-treatment temperature, the heat-treatment pressure, the density of the glass being crystallized, the relative amount(s) of the crystalline phases formed, and the degree of crystallization. The amount of shrinkage can be measured by conventional techniques known in the art, including by dilatometry, Archimedes method, or measuring the dimensions material before and after heat-treatment. In cases, there may be some evolution of volatile species during heat-treatment.

For example, during heat-treatment of some exemplary amorphous materials containing $ZrO_2$ for making glass-ceramics according to present invention, formation of phases such as $La_2Zr_2O_7$, (Zr, M)$O_2$ solid solution with face-centered cubic structure (where M=stabilizing cation), cubic/tetragonal $ZrO_2$, in some cases monoclinic $ZrO_2$, have been observed at temperatures above about 900° C. Although not wanting to be bound by theory, it is believed that zirconia-related phases are the first phases to nucleate from the amorphous material. In amorphous materials that do not contain $ZrO_2$ formation of $Al_2O_3$, $ReAlO_3$ (wherein Re is at least one rare earth cation), $ReAl_{11}O_{18}$, $Re_3Al_5O_{12}$, $Y_3Al_5O_{12}$, etc. phases takes place at temperatures above about 925° C. Typically, crystallite size during this nucleation step is on order of nanometers. For example, crystals as small as 10–15 nanometers have been observed. For at least some embodiments, heat-treatment at about 1300° C. for about 1 hour provides a full crystallization. In general, heat-treatment times for each of the nucleation and crystal growth steps may range of a few seconds (in some embodiments even less than 5 seconds) to several minutes to an hour or more.

The size of the resulting crystals can typically be controlled at least in part by the nucleation and/or crystallization times and/or temperatures. Although it is generally preferred to have small crystals (e.g., on the order not greater than a micrometer, or even not greater than a nanometer), glass-ceramics may be made with larger crystal sizes (e.g., at least 1–10 micrometers, at least 10–25 micrometers, at least 50–100 micrometers, or even grater than 100 micrometers). Although not wanting to be bound by theory, it is generally believed in the art that the finer the size of the crystals (for the same density), the higher the mechanical properties (e.g., hardness and strength) of the ceramic. It is also within the scope of this invention to perform crystallization in such a manner that crystals with needle, whisker or platelet-like morphologies form during heat-treatment. Such crystals could favorably affect fracture toughness, machinability, and other characteristics of the resultant glass-ceramic.

Examples of crystalline phases which may be present in embodiments of glass-ceramics include: $Al_2O_3$ (e.g., ($\alpha$-$Al_2O_3$, or transitional $Al_2O_3$), $Y_2O_3$, REO, $HfO_2$, $ZrO_2$ (e.g., cubic $ZrO_2$ and tetragonal $ZrO_2$), BaO, CaO, $Cr_2O_3$, CoO, $Fe_2O_3$, $GeO_2$, $Li_2O$, MgO, MnO, NiO, $Na_2O$, $P_2O_5$, $Sc_2O_3$, $SiO_2$, SrO, $TeO_2$, $TiO_2$, $V_2O_3$, $Y_2O_3$, ZnO, "complex metal oxides" (including "complex $Al_2O_3$-metal oxide (e.g., complex $Al_2O_3$.REO (e.g., $ReAlO_3$ (e.g., $GdAlO_3$ $LaAlO_3$), $ReAl_{11}O_{18}$ (e.g., $LaAl11O_{18}$,), and $Re_3Al_5O_{12}$ (e.g., $Dy_3Al_5O_{12}$)), complex $Al_2O_3.Y_2O_3$ (e.g., $Y_3Al_5O_{12}$), and complex $ZrO_2$.REO (e.g., $Re_2Zr_2O_7$ (e.g., $La_2Zr_2O_7$))), and combinations thereof.

It is also within the scope of the present invention to substitute a portion of the yttrium and/or aluminum cations in a complex $Al_2O_3$ metal oxide (e.g., complex $Al_2O_3.Y_2O_3$ (e.g., yttrium aluminate exhibiting a garnet crystal structure)) with other cations. For example, a portion of the Al cations in a complex $Al_2O_3.Y_2O_3$ may be substituted with at least one cation of an element selected from the group consisting of: Cr, Ti, Sc, Fe, Mg, Ca, Si, Co, and combinations thereof. For example, a portion of the Y cations in a complex $Al_2O_3.Y_2O_3$ may be substituted with at least one cation of an element selected from the group consisting of: Ce, Dy, Er, Eu, Gd, Ho, La, Lu, Nd, Pr, Sm, Th, Tm, Yb, Fe, Ti, Mn, V, Cr, Co, Ni, Cu, Mg, Ca, Sr, and combinations thereof. Similarly, it is also within the scope of the present invention to substitute a portion of the aluminum cations in alumina. For example, Cr, Ti, Sc, Fe, Mg, Ca, Si, and Co can substitute for aluminum in the alumina. The substitution of cations as described above may affect the properties (e.g., hardness, toughness, strength, thermal conductivity, etc.) of the fused material.

It is also within the scope of the present invention to substitute a portion of the rare earth and/or aluminum cations in a complex $Al_2O_3$.metal oxide (e.g., complex $Al_2O_3$.REO) with other cations. For example, a portion of the Al cations in a complex $Al_2O_3$.REO may be substituted with at least one cation of an element selected from the group consisting of: Cr, Ti, Sc, Fe, Mg, Ca, Si, Co, and combinations thereof. For example, a portion of the Y cations in a complex $Al_2O_3$.REO may be substituted with at least one cation of an element selected from the group consisting of: Y, Fe, Ti, Mn, V, Cr, Co, Ni, Cu, Mg, Ca, Sr, and combinations thereof. Similarly, it is also within the scope of the present invention to substitute a portion of the aluminum cations in alumina. For example, Cr, Ti, Sc, Fe, Mg, Ca, Si, and Co can substitute for aluminum in the alumina. The substitution of cations as described above may affect the properties (e.g., hardness, toughness, strength, thermal conductivity, etc.) of the fused material.

The average crystal size can be determined by the line intercept method according to the ASTM Standard E 112-96 "Standard Test Methods for Determining Average Grain Size". The sample is mounted in mounting resin (such as that obtained under the trade designation "TRANSOPTIC POWDER" from Buehler Ltd., Lake Bluff, Ill.) typically in a cylinder of resin about 2.5 cm in diameter and about 1.9 cm high. The mounted section is prepared using conventional polishing techniques using a polisher (such as that obtained from Buehler Ltd., Lake Bluff, Ill., under the trade designation "ECOMET 3"). The sample is polished for about 3 minutes with a diamond wheel, followed by 5 minutes of polishing with each of 45, 30, 15, 9, 3, and 1-micrometer slurries. The mounted and polished sample is sputtered with a thin layer of gold-palladium and viewed using a scanning electron microscopy (such as the JEOL SEM Model JSM 840A). A typical back-scattered electron (BSE) micrograph of the microstructure found in the sample is used to determine the average crystal size as follows. The number of crystals that intersect per unit length (NL) of a random straight line drawn across the micrograph are counted. The average crystal size is determined from this number using the following equation:

$$\text{Average Crystal Size} = \frac{1.5}{N_L M}$$

Where $N_L$ is the number of crystals intersected per unit length and M is the magnification of the micrograph.

Some embodiments of the present invention include glass-ceramics comprising crystals having at least one of an average crystal size not greater than 150 nanometers.

Some embodiments of the present invention include glass-ceramics comprising crystals, wherein at least 90 (in some embodiments preferably, 95, or even 100) percent by number of the crystals present in such portion have crystal sizes not greater than 200 nanometers.

Some embodiments of the present invention include glass-ceramics comprising $Al_2O_3$, and a first complex $Al_2O_3 \cdot Y_2O_3$, and optionally crystalline $ZrO_2$, and wherein at least one of the $Al_2O_3$, the optional crystalline $ZrO_2$, or the first complex $Al_2O_3 \cdot Y_2O_3$ has an average crystal size not greater than 150 nanometers. In some embodiments preferably, the glass-ceramics further comprise a second, different complex $Al_2O_3 \cdot Y_2O_3$. In some embodiments preferably, the glass-ceramics further comprise a complex $Al_2O_3 \cdot REO$.

Some embodiments of the present invention include glass-ceramics comprising a first complex $Al_2O_3 \cdot Y_2O_3$, a second, different complex $Al_2O_3 \cdot Y_2O_3$, and optionally crystalline $ZrO_2$, and wherein for at least one of the first complex $Al_2O_3 \cdot Y_2O_3$, the second complex $Al_2O_3 \cdot Y_2O_3$, or the optional crystalline $ZrO_2$, at least 90 (in some embodiments preferably, 95, or even 100) percent by number of the crystal sizes thereof are not greater than 200 nanometers. In some embodiments preferably, the glass-ceramics further comprise a second, different complex $Al_2O_3 \cdot Y_2O_3$. In some embodiments preferably, the glass-ceramics further comprise a complex $Al_2O_3 \cdot REO$.

Some embodiments of the present invention include glass-ceramics comprising $Al_2O_3$, a first complex $Al_2O_3 \cdot REO$, and optionally crystalline $ZrO_2$, and wherein at least one of the $Al_2O_3$, the optional crystalline $ZrO_2$, or the first complex $Al_2O_3 \cdot REO$ has an average crystal size not greater than 150 nanometers. In some embodiments preferably, the glass-ceramics further comprise a second, different complex $Al_2O_3 \cdot REO$. In some embodiments preferably, the glass-ceramics further comprise a complex $Al_2O_3 \cdot Y_2O_3$.

Some embodiments of the present invention include glass-ceramics comprising a first complex $Al_2O_3 \cdot REO$, a second, different complex $Al_2O_3 \cdot REO$, and optionally crystalline $ZrO_2$, and wherein for at least one of the first complex $Al_2O_3 \cdot REO$, the second complex $Al_2O_3 \cdot REO$, or the optional crystalline $ZrO_2$, at least 90 (in some embodiments preferably, 95, or even 100) percent by number of the crystal sizes thereof are not greater than 200 nanometers. In some embodiments preferably, the glass-ceramics further comprise a complex $Al_2O_3 \cdot Y_2O_3$.

In some embodiments, glass-ceramics comprise at least 75, 80, 85, 90, 95, 97, 98, 99, or even 100 percent by volume crystallites, wherein the crystallites have an average size of less than 1 micrometer. In some embodiments, glass-ceramics comprise not greater than at least 75, 80, 85, 90, 95, 97, 98, 99, or even 100 percent by volume crystallites, wherein the crystallites have an average size not greater than 0.5 micrometer. In some embodiments, glass-ceramics comprise less than at 75, 80, 85, 90, 95, 97, 98, 99, or even 100 percent by volume crystallites, wherein the crystallites have an average size not greater than 0.3 micrometer. In some embodiments, glass-ceramics comprise less than at least 75, 80, 85, 90, 95, 97, 98, 99, or even 100 percent by volume crystallites, wherein the crystallites have an average size not greater than 0.15 micrometer.

Crystals formed by heat-treating amorphous to provide embodiments of glass-ceramics may be, for example, equiaxed, columnar, or flattened splat-like. The aspect ratio and overall size of whisker, needle, or platelet-like crystals maybe optionally controlled to improve properties.

Although a glass-ceramic may be in the form of a bulk material, it is also within the scope of the present invention to provide composites comprising a glass-ceramic. Such a composite may comprise, for example, a phase or fibers (continuous or discontinuous) or particles (including whiskers) (e.g., metal oxide particles, boride particles, carbide particles, nitride particles, diamond particles, metallic particles, glass particles, and combinations thereof) dispersed in a glass-ceramic, invention or a layered-composite structure (e.g., a gradient of glass-ceramic to amorphous material used to make the glass-ceramic and/or layers of different compositions of glass-ceramics).

Typically, the (true) density, sometimes referred to as specific gravity, of ceramics is typically at least 70% of theoretical density. More desirably, the (true) density of ceramic is at least 75%, 80%, 85%, 90%, 92%, 95%, 96%, 97%, 98%, 99%, 99.5%, or even 100% of theoretical density.

The average hardness of the material of the present invention can be determined as follows. Sections of the material are mounted in mounting resin (obtained under the trade designation "TRANSOPTIC POWDER" from Buehler Ltd., Lake Bluff, Ill.) typically in a cylinder of resin about 2.5 cm in diameter and about 1.9 cm high. The mounted section is prepared using conventional polishing techniques using a polisher (such as that obtained from Buehler Ltd., Lake Bluff, Ill., under the trade designation "ECOMET 3"). The sample is polished for about 3 minutes with a diamond wheel, followed by 5 minutes of polishing with each of 45, 30, 15, 9, 3, and 1-micrometer slurries. The microhardness measurements are made using a conventional microhardness tester (such as that obtained under the trade designation "MITUTOYO MVK-VL" from Mitutoyo Corporation, Tokyo, Japan) fitted with a Vickers indenter using a 100-gram indent load. The microhardness measurements are made according to the guidelines stated in ASTM Test Method E384 Test Methods for Microhardness of Materials (1991), the disclosure of which is incorporated herein by reference.

Additional glasses and glass-ceramics, methods of making same, and methods of making articles containing same, which may be useful in the articles and methods according to the present invention include those disclosed in applications having U.S. application Ser. Nos. 09/922,526, 09/922,527, 09/922,528, and 09/922,530, filed Aug. 2, 2001, now abandoned, U.S. application Ser. No. 10/211,491, filed Aug. 2, 2002; U.S. application Ser. Nos. 10/358,910, 10/358,708, 10/358,855, 10/358,772, and 10/358,765, each filed Feb. 5, 2003: and U.S. Publication Nos. 04-0023078-A1, 04-0020245-A1, 03-0126803-A1, 03-0110708-A1, 03-0110706-A1, 03-0115805-A1, 03-0110707-A1, 03-0110709-A1, 03-0126802-A1, 03-0145525-A1, and 03-0126804-A1, the disclosures of which are incorporated herein by reference.

Dental Materials

The ceramics, glass, and glass-ceramics described above can be incorporated into a hardenable resin to provide useful dental or orthodontic materials such as a paste. These resins are generally thermosetting materials capable of being hardened to form a polymer network including, for example, acrylate-functional materials, methacrylate-functional materials, epoxy-functional materials, vinyl-functional materials, and mixtures thereof. Suitably, the hardenable resin is made from one or more matrix-forming oligomer, monomer, polymer, or blend thereof.

Hardenable resins suitable for use in the dental materials of the present invention include hardenable organic materials having sufficient strength, hydrolytic stability, and non-toxicity to render them suitable for use in the oral environment. Examples of such materials include acrylates, methacrylates, urethanes, carbamoylisocyanurates, epoxies (e.g., those shown in U.S. Pat. No. 3,066,112 (Bowen); U.S. Pat. No. 3,539,533 (Lee II et al.); U.S. Pat. No. 3,629,187 (Waller); U.S. Pat. No. 3,709,866 (Waller); U.S. Pat. No. 3,751,399 (Lee et al.); U.S. Pat. No. 3,766,132 (Lee et al.); U.S. Pat. No. 3,860,556 (Taylor); U.S. Pat. No. 4,002,669 (Gross et al.); U.S. Pat. No. 4,115,346 (Gross et al.); U.S. Pat. No. 4,259,117 (Yamauchi et al.); U.S. Pat. No. 4,292,029 (Craig et al.); U.S. Pat. No. 4,308,190 (Walkowiak et al.); U.S. Pat. No. 4,327,014 (Kawahara et al.); U.S. Pat. No. 4,379,695 (Orlowski et al.); U.S. Pat. No. 4,387,240 (Berg); U.S. Pat. No. 4,404,150 (Tsunekawa et al.)); and mixtures and derivatives thereof.

One class of preferred hardenable materials includes materials having free radically active functional groups. Examples of such materials include monomers having one or more ethylenically unsaturated group, oligomers having one or more ethylenically unsaturated group, polymers having one or more ethylenically unsaturated group, and combinations thereof. Alternatively, the hardenable resin can be selected from materials that include cationically active functional groups. In another alternative, a mixture of hardenable resins that include both cationically curable and free radically curable materials may be used for the dental materials of the invention. In another alternative, the hardenable resin can be a material from the class of materials that includes both cationically active and free radically active functional groups in the same molecule.

In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274 (Boettcher et al.), and acrylated oligomers such as those of U.S. Pat. No. 4,642,126 (Zador); and vinyl compounds such as styrene, diallyl phthalate, divinyl succinate, divinyl adipate and divinylphthalate. Mixtures of two or more of these free radically polymerizable materials can be used if desired.

For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

A variety of visible or near-IR photoinitiator systems may be used for photopolymerization of free-radically polymerizable materials. For example, a photoinitiation system can be selected from systems which initiate polymerization via a two component system of an amine and an α-diketone as described in U.S. Pat. No. 4,071,424 (Dart et al.). Alternatively, the material can be combined with a three component photoinitiator system such as described in U.S. Pat. No. 5,545,676 (Palazzotto et al.). The three component system includes an iodonium salt (e.g., a diaryliodonium salt), a sensitizer, and a donor. Each photoinitiator component is described in U.S. Pat. No. 5,545,676, column 2, line 27, to column 4, line 45.

Other useful free-radical initiators include the class of acylphosphine oxides, as described in European Pat. Application Publ. No. 173,567 (Ying) and U.S. Pat. No. 4,737,593 (Ellrich et al.) and U.S. Pat. No. 6,020,528 (Leppard et al.). Tertiary amine reducing agents may be used in combination with an acylphosphine oxide.

Another free-radical initiator system that can alternatively be used in the dental materials of the invention includes the class of ionic dye-counterion complex initiators including a borate anion and a complementary cationic dye. Borate salt photoinitiators are described, for example, in U.S. Pat. No. 4,772,530 (Gottschalk et al.); U.S. Pat. No. 4,954,414 (Adair et al.); U.S. Pat. No. 4,874,450 (Gottschalk); U.S. Pat. No. 5,055,372 (Shanklin et al.); and U.S. Pat. No. 5,057,393 (Shanklin et al.).

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least about 40° C. and at most about 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

An alternative class of hardenable resins useful in dental materials disclosed in the present application includes materials having cationically active functional groups. Materials having cationically active functional groups include cationically polymerizable epoxies, vinyl ethers, oxetanes, spiro-orthocarbonates, spiro-orthoesters, and the like. Preferred materials having cationically active functional groups are epoxy-functional materials including, for example, those disclosed in U.S. Pat. No. 6,025,406 (Oxman et al.) (e.g., column 2, line 36, to column 4, line 52) and in the documents cited therein.

Optionally, monohydroxy- and polyhydroxy-alcohols may be added to the hardenable resin, as chain-extenders for a hardenable resin having cationically active functional groups, which are preferably epoxy-functional materials.

The hydroxyl-containing material used in the present invention can be any organic material having hydroxyl functionality of at least about 1, and preferably at least about 2. Useful hydroxyl-containing materials are described, for example, in U.S. Pat. No. 5,856,373 (Kaisaki et al.).

For hardening resins including cationically active functional groups, an initiation system can be selected from systems that initiate polymerization via radiation, heat, or redox/auto-cure chemical reactions. For example, epoxy polymerization may be accomplished by the use of thermal curing agents including, for example, anhydrides and amines. A particularly useful example of an anhydride curing agent is cis-1,2-cyclohexanedicarboxylic anhydride.

Alternatively, initiation systems for resins including cationically active functional groups are those that are photo-activated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by, for example, U.S. Pat. No. 4,250,311 (Crivello); U.S. Pat. No. 3,708,296 (Schlesinger); U.S. Pat. No. 4,069,055 (Crivello); U.S. Pat. No. 4,216,288 (Crivello); U.S. Pat. No. 5,084,586 (Farooq); U.S. Pat. No. 5,124,417 (Farooq); U.S. Pat. No. 4,985,340 (Palazzotto et al.); U.S. Pat. No. 5,089,536 (Palazzotto); and U.S. Pat. No. 5,856,373 (Kaisaki et al.).

The cationically-curable materials can be combined with a three component or ternary photoinitiator system, as described above, for example, using an iodonium salt, a sensitizer, and an electron donor. For hardening cationically curable materials, examples of useful aromatic iodonium complex salts are disclosed in U.S. Pat. No. 6,025,406 (Oxman et al.) (e.g., column 5, line 46, to column 6, line 9). Examples of useful sensitizers and electron donors can also be found in U.S. Pat. No. 6,025,406 (e.g., column 6, line 43, to column 9, line 43).

An alternative photoinitiator system for cationic polymerizations includes the use of organometallic complex cations essentially free of metal hydride or metal alkyl functionality selected from those described in U.S. Pat. No. 4,985,340 (Palazzotto et al.).

Alternatively, the hardenable resins may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of a material, which is available under the trade designation "UVR-6105" from Union Carbide, with one equivalent of methacrylic acid. Commercially available materials having epoxy and free-radically active functionalities include materials available under the trade designation "CYCLOMER" (e.g., "CYCLOMER M-100", "M-101", or "A-200") from Daicel Chemical, Japan, and the material available under the trade designation "EBECRYL-3605" from Radcure Specialties.

Photoinitiator compounds are preferably provided in dental materials disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile. A liquid material to be polymerized may be used as a solvent for another liquid or solid material to be polymerized. Solventless compositions can be prepared, for example, by simply dissolving an aromatic iodonium complex salt and sensitizer in an epoxy-functional material/polyol mixture with or without the use of mild heating to facilitate dissolution.

An additional class of hardenable resins include those with pendant acid moieties, which can undergo a setting reaction in the presence of reactive fillers and water. Examples of suitable acid moieties include carboxylates, phosphates, and phosphonates. Examples of suitable compounds include polyacrylic acid; polymers derived from the acrylic acid, methacrylic acid, itaconic acid, maleic acid, glutaconic acid, aconitic acid, citraconic acid, mesaconic acid, fumaric acid, tiglic acid, and combinations thereof; glycerol dimethacrylate phosphate; citric acid dimethacrylate; and propionic acid dimethacrylate and combinations thereof.

The dental materials of the invention may optionally include adjuvants suitable for use in the oral environment including, for example, colorants, flavorants, anti-microbials, fragrances, stabilizers, viscosity modifiers, and fluoride releasing materials. For example, a fluoride releasing glass may be added to dental materials or glasses of the present invention to provide the benefit of long-term release of fluoride in use, for example in the oral cavity. Fluoroaluminosilicate glasses are particularly preferred. Particularly preferred fluoroaluminosilicate glasses are those that have been silanol treated as described, for example, in U.S. Pat. No. 5,332,429 (Mitra et al.). Other suitable adjuvants include, for example, agents that impart fluorescence and/or opalescence.

Method of Making

In one embodiment of the present invention, dental or orthodontic materials are made by mixing a glass, glass-ceramic, or ceramic with a hardenable resin. The dental materials may be provided in various containers including capsules, syringes, foli packages, and cartridges. Dental articles and orthodontic appliances may then be made by forming the dental or orthodontic material into the desired shape and then hardening the hardenable resin.

Typically, the dental material is initially a viscous material, for example, paste, and any of the standard methods for compounding paste may be used to form the composite material. Usually, methods which optimize mixing and minimize the incidence of material discontinuities such as voids and cracks should be instituted. For example, application of vacuum or pressure can be beneficial during any stage of compounding, forming, or curing the paste. Pressure can be applied by various means, including isostatic, uniaxial, centrifugal, impact, or pressurized gas. Heat may optionally be applied at any stage. However, during curing, a uniform temperature in the sample is preferably maintained to minimize internal stresses. During compounding and extrusion, methods that minimize and preferably eliminate material discontinuities such as voids or bubbles are preferred.

Mill blanks of dental or orthodontic material may be made in any desired shape or size, including cylinders, bars, cubes, polyhedra, ovoids, and plates as is known in the art. Molds may be made of a variety of materials, including stainless steel, cobalt alloys, nickel alloys, aluminum alloys, plastic, glass, ceramic, or combinations thereof. Alternatively, a variety of methods for forming and shaping the blanks into any desired configuration can be employed, such as injection molding, centrifugal casting and extrusion. During hardening, compression from springs or other means may optionally be used to reduce internal stresses. Preferably, the outer surface of the blank is smooth and non-tacky.

Hardening may be performed in one or multiple stage methods. In a two-stage process, it is preferred that initial hardening provide a material sufficient to sustain the forces of milling or carving. The second hardening stage, therefore, can be performed on the composite after a dental article or orthodontic appliance is milled from a blank or molded. Such blanks are described in, for example, PCT Publication No. WO 01/13862 A1, incorporated by reference herein.

Hardened blocks may be attached to mounting stubs to facilitate affixation of the blank in a milling machine. Mounting stubs function as handles from which a blank is held by as it is milled by a machine.

Various means of milling the mill blanks of the present invention may be employed to create custom-fit dental prosthetics having a desired shape and morphology. The term "milling" as used herein means abrading, polishing, controlled vaporization, electronic discharge milling (EDM), cutting by water jet or laser or any other method of cutting, removing, shaping, or carving material. While milling the blank by hand using a hand-held tool or instrument is possible, preferably the prosthetic is milled by machine, including computer controlled milling equipment. However, a preferred device to create a prosthetic and achieve the full benefits of the composite material of the present invention is to use a CAD/CAM device capable of milling a blank, such as the Sirona Cerec 2 machine. By using a CAD/CAM milling device, the prosthetic can be fabricated efficiently and with precision. During milling, the contact area may be dry, or it may be flushed with a lubricant. Alternatively, it may be flushed with an air or gas stream. Suitable lubricants are well known in the art, and include water, oils, glycerine, ethylene glycols, and silicones. After machine milling, some degree of finishing, polishing, and adjustment may be necessary to obtain a custom fit in to the mouth and/or aesthetic appearance.

To fabricate blanks of the present invention, the following steps are typically performed: Compound the paste; extrude the paste into a mold; cure the paste via heat, light, microwave, e-beam or chemical cure; remove the blank from its mold and trim excess if necessary; and optionally, mount on a holder stub if necessary. An exemplary method of making the dental mill blank of the present invention comprises the steps of a) mixing a paste comprising a resin and a filler, b) shaping the paste into a desired configuration, c) minimizing material discontinuities from the paste, d) curing the paste into a blank, and e) relieving internal stresses in the blank.

Optionally, where a mold is used to shape the paste, excess paste material can be trimmed from the mold. The cured paste is then removed from the mold. Another optional step that can be performed in making a mill blank is to mount a handle onto the cured paste. Preferably, the handle is a holder stub.

Mill blanks of the present invention may be hardened in a manner such that the material contains minimal internal stresses. This may be accomplished, for example, by application of pressure on the composite material during the hardening process. In the alternative, the avoidance of internal stress imparted by shrinkage may be obtained by selection of mill blank components such that the overall composition exhibits little or no shrinkage during hardening. A preferred curing method entails the use of light to fast harden the composite. During this fast hardening, the temperature may optionally be adjusted and controlled. The fast hardening technique requires a subsequent heat treatment to effectuate stress relief. Heat treatment of a hardened blank requires the blank be heated for a sufficient time and at a sufficient temperature to effectively eliminate internal stresses such that the blank passes a Thermal Shock Test. Preferably, the blank is raised to a temperature of at or above $T_g$ (glass transition temperature) of the resin component of the blank. More preferably, the blank is heated to above $T_g$ and is maintained at that temperature for at least about one-half hour.

An exemplary method of heat treatment for a hardened blank is to place the blank in an oven and raise the oven temperature to about the $T_g$ of the resin component of the blank at a rate of about, for example, 3–5° C./minute. Upon completing heat treatment, the blank is allowed to equilibrate to room temperature either by immersion into room temperature water or by slowly cooling via ambient temperature. Alternatively, the heat treatment may be accomplished by placing the blank in a preheated oven and maintaining the oven temperature at or above $T_g$ for a sufficient time to eliminate internal stresses in the composite blank.

Another method of curing the blanks of the present invention is through a slow hardening using low intensity light. In this technique, hardening is accomplished over a long period of time to minimize internal stresses, such that the resulting hardened blank will pass a Thermal Shock Test. Preferably, the hardening takes place over a time period of about 24 hours, however, it is envisioned that with proper equipment and procedure, curing times may be shorter. Progress of this hardening may be evaluated by ascertaining a sample of the material at predetermined times over the hardening time and evaluating progress of hardening by Barcol Hardness measurement.

Other techniques may be used to relieve the stress of mill blanks of the present invention, including application of energy in a form other than heat, such as sonic or microwave energy.

The ceramics, glasses, and glass-ceramics described in the present application are useful in making dental articles and orthodontic appliances that comprise said ceramics, glasses, and glass-ceramics, as described herein. The ceramics, glasses, and glass-ceramics described herein may be formed, molded, shaped, pressed, etc. into the form of dental articles and orthodontic appliances.

In one embodiment, a method of making a dental article or orthodontic appliance comprises the steps of optionally designing the dental article or the orthodontic appliance; carving a dental or orthodontic mill blank based on said optional design, wherein the dental mill blank comprises a ceramic comprising at least one of the glasses or glass-ceramics described herein. The mill blank or the dental article or orthodontic appliance may be further heat treated as described herein.

In another embodiment, a method of making a dental article or an orthodontic appliance comprising the steps of designing the dental article or the orthodontic appliance, heating a glass above the $T_g$ of the glass such that the glass coalesce (or forms, in the case of a perform) to form a dental article or an orthodontic appliance having a shape based on said optional design; and cooling the coalesced article, wherein the glass comprises at least one of the glasses described herein. The coalesced article may be further heat treated to form an article comprising glass-ceramic. The glass may be in the form of particles, powder, nanoclusters, fibers, flakes, whiskers, block, blank, beads, etc., or combinations thereof.

In another embodiment, a method of making a dental article or orthodontic appliance comprise the steps of optionally designing the dental article or the orthodontic appliance; combining a ceramic, glass, or glass-ceramic with a hardenable resin to form a mixture; forming the dental article or the orthodontic appliance into a shape based on said optional design; hardening said mixture to form the dental article or orthodontic appliance, wherein said ceramic comprises at least one of the glasses, or glass-ceramics described herein.

In another embodiment, the invention provides a method of making a dental article or orthodontic appliance comprising the steps of plasma or thermally spraying particles comprising metal oxide sources onto a suitable substrate such that the particles coalesce to form a shaped article and optionally separating the shaped article or appliance from the substrate, wherein the shaped article comprises at least one of the glasses described herein. Useful substrates include refractory materials that comprise admixtures of silica, silicon carbide, magnesium oxide, mono ammonium phosphate, zircon or aluminum oxide. Metal substrates can also be used in some embodiments.

Uses

The dental materials, glasses, ceramics, and glass-ceramics disclosed in the present application can be used, for example, as dental adhesives, artificial crowns, anterior or posterior fillings, casting materials, cavity liners, pastes, cements, coating compositions, mill blanks, orthodontic appliances, dental articles, restoratives, prostheses, and sealants. For example, restoratives of the invention can be placed directly in the mouth, shaped or formed, and cured (hardened) in-situ, or alternatively, may be fabricated into a prosthesis outside the mouth and subsequently adhered in place inside the mouth.

Practitioners generally desire handling properties in a dental material that allows fast and easy placement, which often translates to time savings. For example, in dental restorative work, it is desirable in some instances that dental materials do not slump (e.g., flow or change in shape), because after a practitioner places the material in the mouth and manipulates the material by contouring and feathering, the practitioner generally wants the imparted shape to remain unchanged until the material is hardened. Materials used for restorative work, having a sufficiently high yield stress generally will not slump; that is, they will not flow under the stress of gravity. The yield stress of a material is the minimum stress required to cause the material to flow, and is described in "Rheology Principles, Measurements, and Applications" by C. W. Macosko, VCH Publishers, Inc., New York, 1994, p. 92. If the stress due to gravity is below the yield stress of the material, then the material will not flow. The stress due to gravity, however, will depend on the mass of dental material being placed as well as the shape.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition. It is also desirable that the dental material not stick to placement instruments, to minimize further alteration of the shape or surface topography.

In an embodiment where the dental material of the invention is a restorative, the dental material preferably has little to no slump, yet easily adapts to, for example, a cavity preparation, and is easily contoured and feathered. Preferably, the dental materials of the invention do not stick to placement instruments, and are advantageously, overall, fast and easy to use in dental procedures such as, for example, restoring tooth structure.

In certain embodiments, the present invention provides dental materials that are capable of being hardened to provide a balance of desirable properties as detailed below (e.g., a low opacity, a low volumetric shrinkage value, a high diametral tensile strength, a high compressive strength, a high retention of gloss upon polishing).

The dental materials of the present invention may be hardened to form, for example, dental articles and orthodontic appliances. In a method of using dental materials including a hardenable resin and ceramics as disclosed in the present application, the dental material may be placed near or on a tooth surface, followed by a manipulation by the practitioner or laboratory to change the topography of the material, then the resin may be hardened. These steps can be followed sequentially or in a different order. For example, where the dental material is a mill blank or an article or appliance, the hardening step is generally completed prior to changing the topography of the dental material. Changing the topography of the dental material can be accomplished in various ways including, for example, carving or manual manipulation using hand held instruments, or by machine or computer aided apparatus (e.g., a CAD/CAM milling machine) in the case of prostheses and mill blanks. Optionally, a finishing step can be performed to polish, finish, or apply a coating on the dental article.

A dental article or orthodontic appliance can be attached to the tooth or bone structure with conventional cements or adhesives or other appropriate means such as glass ionomer, resin cement, zinc phosphate, zinc polycarboxylate, compomer, or resin-modified glass. In addition, material can optionally be added to the milled article or appliance for various purposes including repair, correction, or enhancing esthetics. The additional material may be of one or more different shades or colors. The added material may be composite, ceramic, or metal. A dental porcelain or light-cured composite is preferred.

Strength can be characterized by mechanical measurements such as compressive strength (CS) and diametral tensile strength (DTS). High compressive strength in a dental material is advantageous due to the forces exerted by mastication on dental repairs, replacements, and restorations. Some embodiments of the dental articles and orthodontic appliances disclosed in the present application may exhibit desirable aesthetic qualities including high translucency, high gloss, and high retention of polish after exposure to repetitive abrasion.

Aesthetic quality of a dental article or orthodontic appliance, although a somewhat subjective characteristic (yet well-understood in the dental industry), can be preferably quantified in one aspect, by measuring MacBeth values, in which lower MacBeth values indicate a lower visual opacity. Visual opacity is indicative of dental article's or orthodontic appliance's level of translucency. Low visual opacity is desired so that the hardened dental material will have a life-like luster.

High translucency of a dental article or orthodontic appliance contributes to the aesthetic character and quality of the material. Polishability of such articles and appliances also contributes to the aesthetic character and quality of the material. The ability of such articles and appliances to have a glossy finish and life-like luster upon polishing is highly desirable. An even greater benefit is the ability of such articles and appliances to retain their luster even after repetitive abrasive contact, such as tooth brushing. It has been surprisingly found that some embodiments of dental articles and orthodontic appliances disclosed in the present application have high polishability and are able to retain the polish and luster after repetitive tooth brushing.

The dental materials, dental articles, and orthodontic appliances of the invention can be incorporated into kits, wherein at least one of the articles or appliances is a dental material, dental article or orthodontic appliance of the invention. The kits may also include one or more other components such as a dental mill blank, a bonding agent, a milling lubricant, a color-matching composition suitable for using in an oral environment, an impression material, an instrument, a dental composite, a paste, a dental porcelain, an abrasive, an orthodontic adhesive, an adhesive primer, an appliance positioning tool, instructions for the use of any of these components alone or in combination with any other component or components, and combinations thereof.

Other uses of the ceramics, glasses, and glass-ceramics described herein are as reactive fillers for use in glass ionomers cement as described in U.S. Pat. No. 6,136,885, PCT Publication No. WO 02/085313, and U.S. Pat. No. 5,130,347, incorporated by reference herein; as materials for dental restorations applied by flame spraying as described in U.S. Pat. No. 6,938,990 B1, incorporated by reference herein; in the forming methods described in U.S. Pat. No. 6,342,458 B1, incorporated by reference herein; as dental mill blanks as described in U.S. Pat. No. 6,394,880, incorporated by reference herein; as a porous material for glass infiltration as described in U.S. Pat. Nos. 5,910,273 and 5,250,352, incorporated by reference herein.

EXAMPLES

Raw materials used to make the amorphous glass beads in the Examples were obtained from the following sources unless otherwise indicated

| Raw Material | Source |
|---|---|
| Alumina powder ($Al_2O_3$) | Obtained from Condea Vista, Tucson, AZ, under the trade designation "APA-0.5" |
| Calcium oxide powder (CaO) | Obtained from Alfa Aesar, Ward Hill, MA |
| Calcium fluoride powder ($CaF_2$) | Obtained from Alfa Aesar |
| Cerium oxide powder ($CeO_2$) | Obtained from Rhone-Poulenc, France |
| Chromium oxide powder ($Cr_2O_3$) | Obtained from Aldrich Chemical Company, Milwaukee, WI |
| Dysprosium oxide powder ($Dy_2O_3$) | Obtained from Aldrich Chemical Company |
| Erbium oxide powder ($Er_2O_3$) | Obtained from Aldrich Chemical Company |
| Europium oxide powder ($Eu_2O_3$) | Obtained from Aldrich Chemical Company |
| Gadolinium oxide powder ($Gd_2O_3$) | Obtained from Molycorp Inc., Mountain Pass, CA |
| Hafnium oxide powder ($HfO_2$) | Obtained from Teledyne Wah Chang Albany Company, Albany, OR |
| Iron oxide powder ($Fe_2O_3$) | Obtained from Aldrich Chemical Company |
| Lanthanum oxide powder ($La_2O_3$) | Obtained from Molycorp Inc. |
| Lithium carbonate powder ($Li_2CO_3$) | Obtained from Aldrich Chemical Company |
| Magnesium oxide powder (MgO) | Obtained from Aldrich Chemical Company |
| Manganese oxide powder (MnO) | Obtained from Aldrich Chemical Company |
| Neodymium oxide powder ($Nd_2O_3$) | Obtained from Molycorp Inc. |
| Niobium oxide powder ($Nb_2O_5$) | Obtained from Aldrich Chemical Company |
| Phosphorous oxide powder ($P_2O_5$) | Obtained from Aldrich Chemical Company |
| Silica powder ($SiO_2$) | Obtained from Alfa Aesar |
| Sodium bicarbonate powder ($NaHCO_3$) | Obtained from Aldrich Chemical Company |
| Strontium oxide powder (SrO) | Obtained from Alfa Aesar |
| Tantalum oxide powder ($Ta_2O_5$) | Obtained from Aldrich Chemical Company |
| Titanium dioxide powder ($TiO_2$) | Obtained from Kemira Inc., Savannah, GA |
| Yttrium oxide powder ($Y_2O_3$) | Obtained from H.C. Stark, Newton, MA |
| Yttria-stabilized zirconium oxide powder (Y-PSZ) | Obtained from Zirconia Sales, Inc., Marietta, GA, under the trade designation "HSY-3" |

Description, source, and abbreviations for the materials used to make the photocurable resins described in these Examples.

| Abbreviation | Description | Source |
|---|---|---|
| Bis-GMA | 2,2-Bis[4-(2-hydroxy-3-methacryloyloxy-propoxy)phenyl]propane (CAS No. 1565-94-2) | Made according to generally accepted procedures known in the art |
| UDMA | Diurethane Dimethacrylate (CAS No. 41137-60-4), commercially available as "ROHAMERE 6661-0" | Rohm Tech, Inc., Malden, MA |
| Bis-EMA6 | Ethoxylated (6 mole ethylene oxide) Bisphenol A Dimethacrylate (CAS No. 41637-38-1), commercially available as "Sartomer CD541" | Sartomer Co., Exton, PA |
| TEGDMA | Triethyleneglycol Dimethacrylate | Sartomer Co. |
| CPQ | Camphorquinone | Sigma-Aldrich, St. Louis, MO |
| DPIHFP | Diphenyl Iodonium Hexafluorophosphate | Johnson Matthey, Alpha Aesar Division, Ward Hill, NJ |
| EDMAB | Ethyl 4-Dimethylaminobenzoate | Sigma-Aldrich |
| BHT | 2,6-Di-tert-butyl-4-methylphenol | Sigma-Aldrich |
| NORBLOC 7966 | 2-(2'-Hydroxy-5'-methacryloxyethylphenyl)-H-benzotriazole (CAS No. 96478-09-0) | Janssen Pharmaceuticals, Titusville, PA |
| HEMA | 2-Hydroxethyl Methacrylate | DeGussa Corp./Rohm America Inc. |

Example 1

A polyurethane-lined mill was charged with 819.6 grams (g) of alumina particles ("APA-0.5"), 818 g of lanthanum oxide particles (obtained from Molycorp, Inc.), 362.4 g of yttria-stabilized zirconium oxide particles (with a nominal composition of 94.6 wt-% $ZrO_2$ (+$HfO_2$) and 5.4 wt-% $Y_2O_3$ (obtained under the trade designation "HSY-3" from Zirconia Sales, Inc. of Marietta, Ga.), 1050 g of distilled water and about 2000 g of zirconia milling media (obtained from Tosoh Ceramics, Division of Bound Brook, N.J., under the trade designation "YTZ"). The mixture was milled at 120 revolutions per minute (rpm) for 4 hours to thoroughly mix the ingredients. After the milling, the milling media were removed and the slurry was poured onto a glass ("PYREX") pan where it was dried using a heat-gun. The dried mixture was ground with a mortar and pestle and screened through a 70-mesh screen (212-micrometer opening size). After grinding and screening, some of the particles were fed into a hydrogen/oxygen torch flame. The hydrogen torch used to melt the multiphase particles, thereby generating a melted amorphous glass bead, was a Bethlehem bench burner, delivering hydrogen and oxygen at the following rates. For the inner ring, the hydrogen flow rate was 8 standard liters per minute (SLPM), the oxygen flow rate was 3 SLPM. For the outer ring, the hydrogen flow rate was 23 standard liters per minute (SLPM), the oxygen flow rate was 9.8 SLPM. The dried and sized particles were fed directly into the hydrogen torch flame, where they were melted and transported to an inclined stainless steel surface (approximately 20 inches wide with the slope angle of 45 degrees) with cold water running over (approximately 2 L/min). Obtained in this procedure amorphous beads ranged in size from 30 to 150 microns.

About 50 g of the amorphous beads was placed in a graphite die and hot-pressed using a uniaxial pressing apparatus (obtained under the trade designation "HP-50", Thermal Technology Inc., Brea, Calif.). The hot-pressing was carried out at 960° C. in an argon atmosphere and 13.8 megapascals (MPa) (2000 pounds per square inch (2 ksi)) pressure. The resulting disk was about 48 millimeters in diameter, and about 5 mm thick. Additional hot-press runs were performed to make additional disks. FIG. 1 is an optical photomicrograph of a sectioned bar (2-mm thick) of the hot-pressed material demonstrating its transparency.

The Young's Modulus (E) of the resulting hot-pressed glass material was measured using a ultrasonic test system (obtained from Nortek, Richland, Wash., under the trade designation "NDT-140"), and found to be within a range of about 130–150 GPa.

The average microhardnesses of the resulting hot-pressed material was determined as follows. Pieces of the hot-pressed material (about 2 to 5 millimiters in size) were mounted in mounting resin (obtained under the trade designation "EPOMET" from Buehler Ltd., Lake Bluff, Ill.). The resulting cylinder of resin was about 2.5 cm (1 inch) in diameter and about 1.9 cm (0.75 inch) tall (i.e., high). The mounted samples were polished using a conventional grinder/polisher (obtained under the trade designation "EPOMET" from Buehler Ltd.) and conventional diamond slurries with the final polishing step using a 1-micrometer diamond slurry (obtained under the trade designation "METADI" from Buehler Ltd.) to obtain polished cross-sections of the sample.

The microhardness measurements were made using a conventional microhardness tester (obtained under the trade designation "MITUTOYO MVK-VL" from Mitutoyo Corporation, Tokyo, Japan) fitted with a Vickers indenter using a 500-gram indent load. The microhardness measurements were made according to the guidelines stated in ASTM Test Method E384 Test Methods for Microhardness of Materials' (1991), the disclosure of which is incorporated herein by reference. The microhardness values were an average of 20 measurements. The average microhardness of the hot-pressed material was about 8.3 GPa.

The average indentation toughness of the hot-pressed material was calculated by measuring the crack lengths extending from the apices of the vickers indents made using a 500 g load with a microhardness tester (obtained under the trade designation "MITUTOYO MVK-VL" from Mitutoyo Corporation, Tokyo, Japan). Indentation toughness ($K_{IC}$) was calculated according to the equation:

$$K_{IC} = 0.016 \, (E/H)^{1/2} (P/c)^{3/2}$$

wherein: E=Young's Modulus of the material;
H=Vickers hardness;
P=Newtons of force on the indenter;
c=Length of the crack from the center of the indent to its end.

Samples for the toughness were prepared as described above for the microhardness test. The reported indentation toughness values are an average of 5 measurements. Crack (c) were measured with a digital caliper on photomicrographs taken using a scanning electron microscope ("JEOL SEM" (Model JSM 6400)). The average indentation toughness of the hot-pressed material was 1.4 MPa·m$^{1/2}$.

The thermal expansion coefficient of the hot-pressed material was measured using a thermal analyser (obtained from Perkin Elmer, Shelton, Conn., under the trade designation "PERKIN ELMER THERMAL ANALYSER"). The average thermal expansion coefficient was 7.6×10$^{-6}$/° C.

The thermal conductivity of the hot-pressed material was measured according to an ASTM Standard "D 5470-95, Test Method A" (1995), the disclosure of which is incorporated herein by reference. The average thermal conductivity was 1.15 W/m·K.

The translucent disk of hot-pressed $La_2O_3$—$Al_2O_3$—$ZrO_2$ glass was heat-treated in a furnace (an electrically heated furnace (obtained under the trade designation "Model KKSK-666-3100" from Keith Furnaces of Pico Rivera, Calif.)) as follows. The disk was first heated from room temperature (about 25° C.) to about 900° C. at a rate of about 10° C./min and then held at 900° C. for about 1 hour. Next, the disk was heated from about 900° C. to about 1300° C. at a rate of about 10° C./min and then held at 1300° C. for about 1 hour, before cooling back to room temperature by turning off the furnace. Additional run was performed as described above except the final temperature was 1400° C.

FIG. 2(a,b) is a scanning electron microscope (SEM) photomicrograph of a polished section of Example 1 materials heat-treated at 1300° C. and 1400° C., respectively, showing the fine crystalline nature of the material and the influence of the processing conditions on the crystallinity of the product. The polished section was prepared using conventional mounting and polishing techniques.

Based on powder x-ray diffraction of a portion of heat-treated Example 1 material and examination of the polished sample using SEM in the backscattered mode, it is believed that the dark portions in the photomicrograph were crystalline $LaAl_{11}O_{18}$, the gray portions crystalline $LaAlO_3$, and the white portions crystalline cubic/tetragonal $ZrO_2$. The Young's Modulus (E) of the heat-treated material was measured using an ultrasonic test system (obtained from Nortek, Richland, Wash., under the trade designation "NDT-140"), and found to be about 260 GPa. The average microhardness of the heat-treated at 1300° C. material was determined as described above was found to be 18.3 GPa. The average fracture toughness ($K_{Ic}$) of the heat-treated at 1300° C. material was determined as described above and was found to be 3.4 Mpa·m$^{1/2}$.

The average microhardness of the heat-treated at 1400° C. material was determined to be 15.4 GPa. The average fracture toughness ($K_{Ic}$) of the heat-treated at 1400° C. material was determined to be 5.7 Mpa·m$^{1/2}$.

The crush strength was measured for 90–125 micron amorphous beads according to the test procedure described in U.S. Pat. No. 4,772,511 (Wood et al.). (See Table I for crystallization conditions.) For comparison purposes, the crush strength of YTZ (yttria tetragonal zirconia) crystalline beads (100 microns in size) obtained from Tosoh Ceramics was also measured. Table I demonstrates the superior strength of beaded glass-ceramic materials of this invention compared to $ZrO_2$.

TABLE I

Crush Strength of Beaded Glass-ceramic Materials of the Invention

| Material | Heat-treatment, °C. | Appearance | Crush-strength, MPa |
|---|---|---|---|
| Example 1 | 1225 | Hazy/Clear | 1601 |
| Example 1 | 1300 | Opaque | 2282 |
| $ZrO_2$ ("YTZ") | None | Opaque | 1234 |

Examples 2–62

Examples 2–62 beads were prepared as described in Example 1, except the raw materials and the amounts used are listed in Table II, below, and milling of raw materials was carried out in 90 ml of isopropyl alcohol with 200 g of the zirconia media (obtained from Tosoh Ceramics, Division of Bound Brook, N.J., under "YTZ" designation) at 120 rpm for 24 hours.

TABLE II

Bead Formulations

| Example | Weight Percent of Components | Powder Batch Amounts, g |
|---|---|---|
| 2 | $La_2O_3$: 45.06 | $La_2O_3$: 22.53 |
|   | $Al_2O_3$: 34.98 | $Al_2O_3$: 17.49 |
|   | $ZrO_2$: 19.96 | $ZrO_2$: 9.98 |
| 3 | $La_2O_3$: 42.29 | $La_2O_3$: 21.15 |
|   | $Al_2O_3$: 38.98 | $Al_2O_3$: 19.49 |
|   | $ZrO_2$: 8.73 | $ZrO_2$: 9.37 |
| 4 | $La_2O_3$: 39.51 | $La_2O_3$: 19.76 |
|   | $Al_2O_3$: 42.98 | $Al_2O_3$: 21.49 |
|   | $ZrO_2$: 17.51 | $ZrO_2$: 8.76 |
| 5 | $La_2O_3$: 36.74 | $La_2O_3$: 18.37 |
|   | $Al_2O_3$: 46.98 | $Al_2O_3$: 23.49 |
|   | $ZrO_2$: 16.28 | $ZrO_2$: 8.14 |
| 6 | $La_2O_3$: 38.65 | $La_2O_3$: 19.33 |
|   | $Al_2O_3$: 38.73 | $Al_2O_3$: 19.37 |
|   | $ZrO_2$: 22.62 | $ZrO_2$: 11.31 |
| 7 | $La_2O_3$: 40.15 | $La_2O_3$: 20.08 |
|   | $Al_2O_3$: 40.23 | $Al_2O_3$: 20.12 |
|   | $ZrO_2$: 19.62 | $ZrO_2$: 9.81 |
| 8 | $La_2O_3$: 43.15 | $La_2O_3$: 21.58 |
|   | $Al_2O_3$: 43.23 | $Al_2O_3$: 21.62 |
|   | $ZrO_2$: 13.62 | $ZrO_2$: 6.81 |
| 9 | $La_2O_3$: 35.35 | $La_2O_3$: 17.68 |
|   | $Al_2O_3$: 48.98 | $Al_2O_3$: 24.49 |
|   | $ZrO_2$: 15.66 | $ZrO_2$: 7.83 |
| 10 | $La_2O_3$: 32.58 | $La_2O_3$: 16.20 |
|    | $Al_2O_3$: 52.98 | $Al_2O_3$: 26.49 |
|    | $ZrO_2$: 14.44 | $ZrO_2$: 7.22 |
| 11 | $La_2O_3$: 31.20 | $La_2O_3$: 15.60 |
|    | $Al_2O_3$: 54.98 | $Al_2O_3$: 27.49 |
|    | $ZrO_2$: 13.82 | $ZrO_2$: 6.91 |
| 12 | $La_2O_3$: 28.43 | $La_2O_3$: 14.22 |
|    | $Al_2O_3$: 58.98 | $Al_2O_3$: 29.49 |
|    | $ZrO_2$: 12.59 | $ZrO_2$: 6.30 |
| 13 | $La_2O_3$: 26.67 | $La_2O_3$: 13.34 |
|    | $Al_2O_3$: 55.33 | $Al_2O_3$: 27.67 |
|    | $ZrO_2$: 18.00 | $ZrO_2$: 9.00 |

TABLE II-continued

Bead Formulations

| Example | Weight Percent of Components | Powder Batch Amounts, g |
|---|---|---|
| 14 | $ZrO_2$: 5.00 | $ZrO_2$: 2.50 |
|    | $La_2O_3$: 86.50 | $La_2O_3$: 43.25 |
|    | $Al_2O_3$: 8.50 | $Al_2O_3$: 4.25 |
| 15 | $ZrO_2$: 10.00 | $ZrO_2$: 5.00 |
|    | $La_2O_3$: 81.90 | $La_2O_3$: 40.95 |
|    | $Al_2O_3$: 8.10 | $Al_2O_3$: 4.05 |
| 16 | $CeO_2$: 41.40 | $CeO_2$: 20.70 |
|    | $Al_2O_3$: 40.60 | $Al_2O_3$: 20.30 |
|    | $ZrO_2$: 18.00 | $ZrO_2$: 9.00 |
| 17 | $Al_2O_3$: 41.00 | $Al_2O_3$: 20.50 |
|    | $ZrO_2$: 17.00 | $ZrO_2$: 8.50 |
|    | $Eu_2O_3$: 41.00 | $Eu_2O_3$: 20.50 |
| 18 | $Al_2O_3$: 41.00 | $Al_2O_3$: 20.50 |
|    | $ZrO_2$: 18.00 | $ZrO_2$: 9.00 |
|    | $Gd_2O_3$: 41.00 | $Gd_2O_3$: 20.50 |
| 19 | $Al_2O_3$: 41.00 | $Al_2O_3$: 20.50 |
|    | $ZrO_2$: 18.00 | $ZrO_2$: 9.00 |
|    | $Dy_2O_3$: 41.00 | $Dy_2O_3$: 20.50 |
| 20 | $Al_2O_3$: 40.90 | $Al_2O_3$: 20.45 |
|    | $Er_2O_3$: 40.90 | $Er_2O_3$: 20.45 |
|    | $ZrO_2$: 18.20 | $ZrO_2$: 9.10 |
| 21 | $La_2O_3$: 35.00 | $La_2O_3$: 17.50 |
|    | $Al_2O_3$: 40.98 | $Al_2O_3$: 20.49 |
|    | $ZrO_2$: 18.12 | $ZrO_2$: 9.06 |
|    | $Nd_2O_3$: 5.00 | $Nd_2O_3$: 2.50 |
| 22 | $La_2O_3$: 35.00 | $La_2O_3$: 17.50 |
|    | $Al_2O_3$: 40.98 | $Al_2O_3$: 20.49 |
|    | $ZrO_2$: 18.12 | $ZrO_2$: 9.06 |
|    | $CeO_2$: 5.00 | $CeO_2$: 2.50 |
| 23 | $La_2O_3$: 35.00 | $La_2O_3$: 17.50 |
|    | $Al_2O_3$: 40.98 | $Al_2O_3$: 20.49 |
|    | $ZrO_2$: 18.12 | $ZrO_2$: 9.06 |
|    | $Eu_2O_3$: 5.00 | $Eu_2O_3$: 2.50 |
| 24 | $La_2O_3$: 35.00 | $La_2O_3$: 17.50 |
|    | $Al_2O_3$: 40.98 | $Al_2O_3$: 20.49 |
|    | $ZrO_2$: 18.12 | $ZrO_2$: 9.06 |
|    | $Er_2O_3$: 5.00 | $Er_2O_3$: 2.50 |
| 25 | $HfO_2$: 35.50 | $HfO_2$: 17.75 |
|    | $Al_2O_3$: 32.50 | $Al_2O_3$: 16.25 |
|    | $La_2O_3$: 32.50 | $La_2O_3$: 16.25 |
| 26 | $La_2O_3$: 41.7 | $La_2O_3$: 20.85 |
|    | $Al_2O_3$: 35.4 | $Al_2O_3$: 17.70 |
|    | $ZrO_2$: 16.9 | $ZrO_2$: 8.45 |
|    | MgO: 6.0 | MgO: 3.00 |
| 27 | $La_2O_3$: 39.90 | $La_2O_3$: 19.95 |
|    | $Al_2O_3$: 33.90 | $Al_2O_3$: 16.95 |
|    | $ZrO_2$: 16.20 | $ZrO_2$: 8.10 |
|    | MgO: 10.00 | MgO: 5.00 |
| 28 | $La_2O_3$: 43.02 | $La_2O_3$: 21.51 |
|    | $Al_2O_3$: 36.50 | $Al_2O_3$: 18.25 |
|    | $ZrO_2$: 17.46 | $ZrO_2$: 8.73 |
|    | $Li_2CO_3$: 3.00 | $Li_2CO_3$: 1.50 |
| 29 | $La_2O_3$: 41.70 | $La_2O_3$: 20.85 |
|    | $Al_2O_3$: 35.40 | $Al_2O_3$: 17.70 |
|    | $ZrO_2$: 16.90 | $ZrO_2$: 8.45 |
|    | $Li_2CO_3$: 6.00 | $Li_2CO_3$: 3.00 |
| 30 | $La_2O_3$: 38.80 | $La_2O_3$: 19.40 |
|    | $Al_2O_3$: 40.70 | $Al_2O_3$: 20.35 |
|    | $ZrO_2$: 17.50 | $ZrO_2$: 8.75 |
|    | $Li_2CO_3$: 3.00 | $Li_2CO_3$: 1.50 |
| 31 | $La_2O_3$: 43.02 | $La_2O_3$: 21.51 |
|    | $Al_2O_3$: 36.50 | $Al_2O_3$: 18.25 |
|    | $ZrO_2$: 17.46 | $ZrO_2$: 8.73 |
|    | $TiO_2$: 3.00 | $TiO_2$: 1.50 |
| 32 | $La_2O_3$: 43.02 | $La_2O_3$: 21.51 |
|    | $Al_2O_3$: 36.50 | $Al_2O_3$: 18.25 |
|    | $ZrO_2$: 17.46 | $ZrO_2$: 8.73 |
|    | $NaHCO_3$: 3.0 | $NaHCO_3$: 1.50 |
| 33 | $La_2O_3$: 42.36 | $La_2O_3$: 21.18 |
|    | $Al_2O_3$: 35.94 | $Al_2O_3$: 17.97 |
|    | $ZrO_2$: 17.20 | $ZrO_2$: 8.60 |
|    | $NaHCO_3$: 4.50 | $NaHCO_3$: 2.25 |
| 34 | $La_2O_3$: 43.02 | $La_2O_3$: 21.51 |
|    | $Al_2O_3$: 36.50 | $Al_2O_3$: 18.25 |

TABLE II-continued

Bead Formulations

| Example | Weight Percent of Components | Powder Batch Amounts, g |
|---|---|---|
|  | $ZrO_2$: 17.46 | $ZrO_2$: 8.73 |
|  | MgO: 1.50 | MgO: 0.75 |
|  | $NaHCO_3$: 1.50 | $NaHCO_3$: 0.75 |
|  | $TiO_2$: 1.50 | $TiO_2$: 0.75 |
| 35 | $La_2O_3$: 43.00 | $La_2O_3$: 21.50 |
|  | $Al_2O_3$: 32.00 | $Al_2O_3$: 16.0 |
|  | $ZrO_2$: 12.00 | $ZrO_2$: 6.00 |
|  | $SiO_2$: 13.00 | $SiO_2$: 6.50 |
| 36 | $Y_2O_3$: 28.08 | $Y_2O_3$: 14.04 |
|  | $Al_2O_3$: 58.48 | $Al_2O_3$: 29.24 |
|  | $ZrO_2$: 13.44 | $ZrO_2$: 6.72 |
| 37 | $Y_2O_3$: 27.6 | $Y_2O_3$: 13.80 |
|  | $Al_2O_3$: 57.50 | $Al_2O_3$: 23.75 |
|  | $ZrO_2$: 14.90 | $ZrO_2$: 7.45 |
| 38 | $Y_2O_3$: 27.44 | $Y_2O_3$: 13.72 |
|  | $Al_2O_3$: 57.14 | $Al_2O_3$: 28.57 |
|  | $ZrO_2$: 15.43 | $ZrO_2$: 7.71 |
| 39 | $Y_2O_3$: 28.70 | $Y_2O_3$: 14.35 |
|  | $Al_2O_3$: 55.70 | $Al_2O_3$: 27.85 |
|  | $ZrO_2$: 15.50 | $ZrO_2$: 7.75 |
| 40 | $Y_2O_3$: 19.00 | $Y_2O_3$: 9.50 |
|  | $Al_2O_3$: 51.00 | $Al_2O_3$: 25.50 |
|  | $ZrO_2$: 17.90 | $ZrO_2$: 8.95 |
|  | $La_2O_3$: 12.10 | $La_2O_3$: 6.05 |
| 41 | $Y_2O_3$: 19.30 | $Y_2O_3$: 9.65 |
|  | $Al_2O_3$: 50.50 | $Al_2O_3$: 25.25 |
|  | $ZrO_2$: 17.80 | $ZrO_2$: 8.90 |
|  | $Nd_2O_3$: 12.40 | $Nd_2O_3$: 6.20 |
| 42 | $Y_2O_3$: 19.10 | $Y_2O_3$: 9.55 |
|  | $Al_2O_3$: 50 | $Al_2O_3$: 25.00 |
|  | $ZrO_2$: 17.80 | $ZrO_2$: 8.90 |
|  | $Gd_2O_3$: 13.10 | $Gd_2O_3$: 6.55 |
| 43 | $Y_2O_3$: 19.00 | $Y_2O_3$: 9.50 |
|  | $Al_2O_3$: 49.70 | $Al_2O_3$: 24.85 |
|  | $ZrO_2$: 17.55 | $ZrO_2$: 8.77 |
|  | $Er_2O_3$: 13.80 | $Er_2O_3$: 6.90 |
| 44 | $Y_2O_3$: 27.40 | $Y_2O_3$: 13.70 |
|  | $Al_2O_3$: 50.30 | $Al_2O_3$: 25.15 |
|  | $ZrO_2$: 17.80 | $ZrO_2$: 8.90 |
|  | $Li_2CO_3$: 4.50 | $Li_2CO_3$: 2.25 |
| 45 | $HfO_2$: 20.08 | $HfO_2$: 14.04 |
|  | $Al_2O_3$: 46.55 | $Al_2O_3$: 23.27 |
|  | $Y_2O_3$: 25.37 | $Y_2O_3$: 12.67 |
| 46 | $Y_2O_3$: 27.40 | $Y_2O_3$: 13.7 |
|  | $Al_2O_3$: 50.30 | $Al_2O_3$: 25.15 |
|  | $ZrO_2$: 17.80 | $ZrO_2$: 8.90 |
|  | MgO: 4.50 | MgO: 2.25 |
| 47 | $Y_2O_3$: 27.40 | $Y_2O_3$: 13.70 |
|  | $Al_2O_3$: 50.30 | $Al_2O_3$: 25.15 |
|  | $ZrO_2$: 17.80 | $ZrO_2$: 8.90 |
|  | CaO: 4.50 | CaO: 2.25 |
| 48 | $Y_2O_3$: 27.40 | $Y_2O_3$: 13.70 |
|  | $Al_2O_3$: 50.30 | $Al_2O_3$: 25.15 |
|  | $ZrO_2$: 17.80 | $ZrO_2$: 8.90 |
|  | $TiO_2$: 4.50 | $TiO_2$: 2.25 |
| 49 | $Y_2O_3$: 27.40 | $Y_2O_3$: 13.70 |
|  | $Al_2O_3$: 50.30 | $Al_2O_3$: 25.15 |
|  | $ZrO_2$: 17.80 | $ZrO_2$: 8.90 |
|  | $NaHCO_3$: 4.50 | $NaHCO_3$: 2.25 |
| 50 | $Y_2O_3$: 27.40 | $Y_2O_3$: 13.70 |
|  | $Al_2O_3$: 50.30 | $Al_2O_3$: 25.15 |
|  | $ZrO_2$: 17.80 | $ZrO_2$: 8.90 |
|  | $SiO_2$: 4.50 | $SiO_2$: 2.25 |
| 51 | $Al_2O_3$: 31.20 | $Al_2O_3$: 15.60 |
|  | $La_2O_3$: 34.00 | $La_2O_3$: 17.00 |
|  | $ZrO_2$: 14.80 | $ZrO_2$: 7.40 |
|  | $CaF_2$: 20.00 | $CaF_2$: 10.00 |
| 52 | $Al_2O_3$: 35.73 | $Al_2O_3$: 17.87 |
|  | $La_2O_3$: 42.17 | $La_2O_3$: 21.08 |
|  | $ZrO_2$: 17.10 | $ZrO_2$: 8.55 |
|  | $P_2O_5$: 5.00 | $P_2O_5$: 2.50 |
| 53 | $Al_2O_3$: 35.73 | $Al_2O_3$: 17.87 |
|  | $La_2O_3$: 42.17 | $La_2O_3$: 21.08 |
|  | $ZrO_2$: 17.10 | $ZrO_2$: 8.55 |
|  | $Nb_2O_5$: 5.00 | $Nb_2O_5$: 2.50 |
| 54 | $Al_2O_3$: 35.73 | $Al_2O_3$: 17.87 |
|  | $La_2O_3$: 42.17 | $La_2O_3$: 21.08 |
|  | $ZrO_2$: 17.10 | $ZrO_2$: 8.55 |
|  | $Ta_2O_5$: 5.00 | $Ta_2O_5$: 2.50 |
| 55 | $Al_2O_3$: 35.73 | $Al_2O_3$: 17.87 |
|  | $La_2O_3$: 42.17 | $La_2O_3$: 21.08 |
|  | $ZrO_2$: 17.10 | $ZrO_2$: 8.55 |
|  | SrO: 5.00 | SrO: 2.50 |
| 56 | $Al_2O_3$: 35.73 | $Al_2O_3$: 17.87 |
|  | $La_2O_3$: 42.17 | $La_2O_3$: 21.08 |
|  | $ZrO_2$: 17.10 | $ZrO_2$: 8.55 |
|  | $Mn_2O_3$: 5.00 | $Mn_2O_3$: 2.50 |
| 57 | $Al_2O_3$: 36.50 | $Al_2O_3$: 18.25 |
|  | $La_2O_3$: 43.04 | $La_2O_3$: 21.52 |
|  | $ZrO_2$: 17.46 | $ZrO_2$: 8.73 |
|  | $Fe_2O_3$: 3.00 | $Fe_2O_3$: 1.50 |
| 58 | $Al_2O_3$: 36.50 | $Al_2O_3$: 18.25 |
|  | $La_2O_3$: 43.04 | $La_2O_3$: 21.52 |
|  | $ZrO_2$: 17.46 | $ZrO_2$: 8.73 |
|  | $Cr_2O_3$: 3.00 | $Cr_2O_3$: 1.50 |
| 59 | CaO: 36.00 | CaO: 18.00 |
|  | $Al_2O_3$: 44.00 | $Al_2O_3$: 22.00 |
|  | $ZrO_2$: 20.00 | $ZrO_2$: 10.00 |
| 60 | $La_2O_3$: 40.90 | $La_2O_3$: 20.45 |
|  | $Al_2O_3$: 40.98 | $Al_2O_3$: 20.49 |
|  | $ZrO_2$: 18.12 | $ZrO_2$: 9.06 |
| 61 | SrO: 22.95 | SrO: 11.47 |
|  | $Al_2O_3$: 62.05 | $Al_2O_3$: 31.25 |
|  | $ZrO_2$: 15.00 | $ZrO_2$: 7.50 |
| 62 | $La_2O_3$: 50.00 | $La_2O_3$: 25.00 |
|  | $Al_2O_3$: 22.00 | $Al_2O_3$: 11.00 |
|  | $SiO_2$: 28.00 | $SiO_2$: 14.00 |

Various properties/characteristics of some Example 1–62 material were measured as follows. Powder x-ray diffraction (using an x-ray diffractometer (obtained under the trade designation "PHILLIPS XRG 3100" from PHILLIPS, Mahwah, N.J.) with copper $K_{\alpha 1}$ radiation of 1.54050 Angstrom)) was used to qualitatively measure phases present in example materials. The presence of broad diffused intensity peak was taken as an indication of glassy nature of a material. The existence of both broad peak and well-defined peaks was taken as an indication of existence of crystalline matter within an amorphous matrix. Phases detected in various examples are reported in Table III, below.

TABLE III

Physical Characteristics of Beads of Examples 1–62

| Example | Phases detected via x-ray diffraction | Color | Glass Transition Temperature ($T_g$, °C.) | Crystallization Temperature ($T_x$, °C.) | Hot-Pressing Temperature (°C.) |
|---|---|---|---|---|---|
| 1 | Amorphous* | Clear | 834 | 932 | 960 |
| 2 | Amorphous* | Clear | 837 | 936 | 960 |
| 3 | Amorphous* | Clear | 831 | 935 | — |
| 4 | Amorphous* | Clear | 843 | 928 | — |
| 5 | Amorphous* | Clear | 848 | 920 | 960 |
| 6 | Amorphous* | Clear | 850 | 923 | — |
| 7 | Amorphous* | Clear | 849 | 930 | — |
| 8 | Amorphous* | Clear | 843 | 932 | — |
| 9 | Amorphous* | Clear | 856 | 918 | 960 |
| 10 | Amorphous* and crystalline | Clear/milky | 858 | 914 | 965 |
| 11 | Amorphous* and crystalline | Clear/milky | 859 | 914 | — |
| 12 | Amorphous* and crystalline | Clear/milky | 862 | 912 | — |
| 13 | Amorphous* and crystalline | Clear/milky | 875 | 908 | — |
| 14 | Crystalline and amorphous | Milky/clear | — | — | — |
| 15 | Crystalline and amorphous | Milky/clear | — | — | — |
| 16 | Amorphous* and crystalline | Brown | 838 | 908 | 960 |
| 17 | Amorphous* | Intense yellow/mustard | 874 | 921 | 975 |
| 18 | Amorphous* | Clear | 886 | 933 | 985 |
| 19 | Amorphous* | Greenish | 881 | 935 | 985 |
| 20 | Amorphous* | Intense pink | 885 | 934 | |
| 21 | Amorphous* | Blue/pink fluorescent | 836 | 930 | 965 |
| 22 | Amorphous* | Yellow | 831 | 934 | 965 |
| 23 | Amorphous* | Yellow/gold | 838 | 929 | — |
| 24 | Amorphous* | Pink | 841 | 932 | — |
| 25 | Amorphous* | Light green | 828 | 937 | 960 |
| 26 | Amorphous* | Clear | 795 | 901 | 950 |
| 27 | Amorphous* | Clear | 780 | 870 | — |
| 28 | Amorphous* | Clear | 816 | 942 | 950 |
| 29 | Amorphous* | Clear | 809 | 934 | 950 |
| 30 | Amorphous* | Clear/greenish | 840 | 922 | 950 |
| 31 | Amorphous* | Clear | 836 | 934 | 950 |
| 32 | Amorphous* | Clear | 832 | 943 | 950 |
| 33 | Amorphous* | clear | 830 | 943 | 950 |
| 34 | Amorphous* | Clear/some green | 818 | 931 | 950 |
| 35 | Amorphous* | Clear | 837 | 1001 | 970 |
| 36 | Amorphous* and Crystalline | Clear/milky | 874 | 932 | 980 |
| 37 | Amorphous* and Crystalline | Clear/milky | 871 | 934 | — |
| 38 | Amorphous* and Crystalline | Clear/milky | 874 | 937 | — |
| 39 | Amorphous* and Crystalline | Clear/milky | 870 | 942 | — |
| 40 | Amorphous* | Clear | 843 | 938 | 970 |
| 41 | Amorphous* | Blue/pink fluorescent | 848 | 934 | 970 |
| 42 | Amorphous* and Crystalline | Clear/milky | 880 | 943 | — |
| 43 | Amorphous* and Crystalline | Pink | 876 | 936 | — |
| 44 | Amorphous* | Clear | 821 | 927 | 970 |
| 45 | Amorphous* and Crystalline | Clear/Greenish | 867 | 948 | — |

TABLE III-continued

Physical Characteristics of Beads of Examples 1–62

| Example | Phases detected via x-ray diffraction | Color | Glass Transition Temperature ($T_g$, °C.) | Crystallization Temperature ($T_x$, °C.) | Hot-Pressing Temperature (°C.) |
|---|---|---|---|---|---|
| 46 | Amorphous* and Crystalline | Clear/milky | 869 | 934 | — |
| 47 | Amorphous* | Clear | 845 | 922 | 970 |
| 48 | Amorphous* and Crystalline | Clear/milky | 870 | 933 | — |
| 49 | Amorphous* | Clear | 831 | 916 | 970 |
| 50 | Amorphous* | Clear | 826 | 926 | 970 |
| 51 | Amorphous* | Clear | — | 676 | — |
| 52 | Amorphous* | Clear | 857 | 932 | — |
| 53 | Amorphous* | Clear | — | — | — |
| 54 | Amorphous* | Clear | — | — | — |
| 55 | Amorphous* | Clear | — | — | — |
| 56 | Amorphous* | Clear/Brown | — | — | — |
| 57 | Amorphous* | Clear/grey | — | — | — |
| 58 | Amorphous* | Clear/Green | — | — | — |
| 59 | Amorphous* | Clear | 851 | 977 | 975 |
| 60 | Amorphous* | Clear | 839 | 932 | 965 |
| 61 | Amorphous* | Clear | 875 | 934 | 975 |
| 62 | Amorphous* | Clear | 842 | 1085 | 1050** |

*glass, as the example has a $T_g$
**sintering conducted without application of pressure For differential thermal analysis (DTA), a material was screened to retain amorphous beads (microspheres) in the 90–125 micrometer size range. DTA runs were made (using an instrument obtained from Netzsch Instruments, Selb, Germany, under the trade designation "NETZSCH STA 409 DTA/TGA"). The amount of each screened sample placed in the 100 microliter $Al_2O_3$ sample holder was 400 milligrams. Each sample was heated in static air at a rate of 10° C./minute from room temperature (about 25° C.) to 1200° C.

Figure 3:
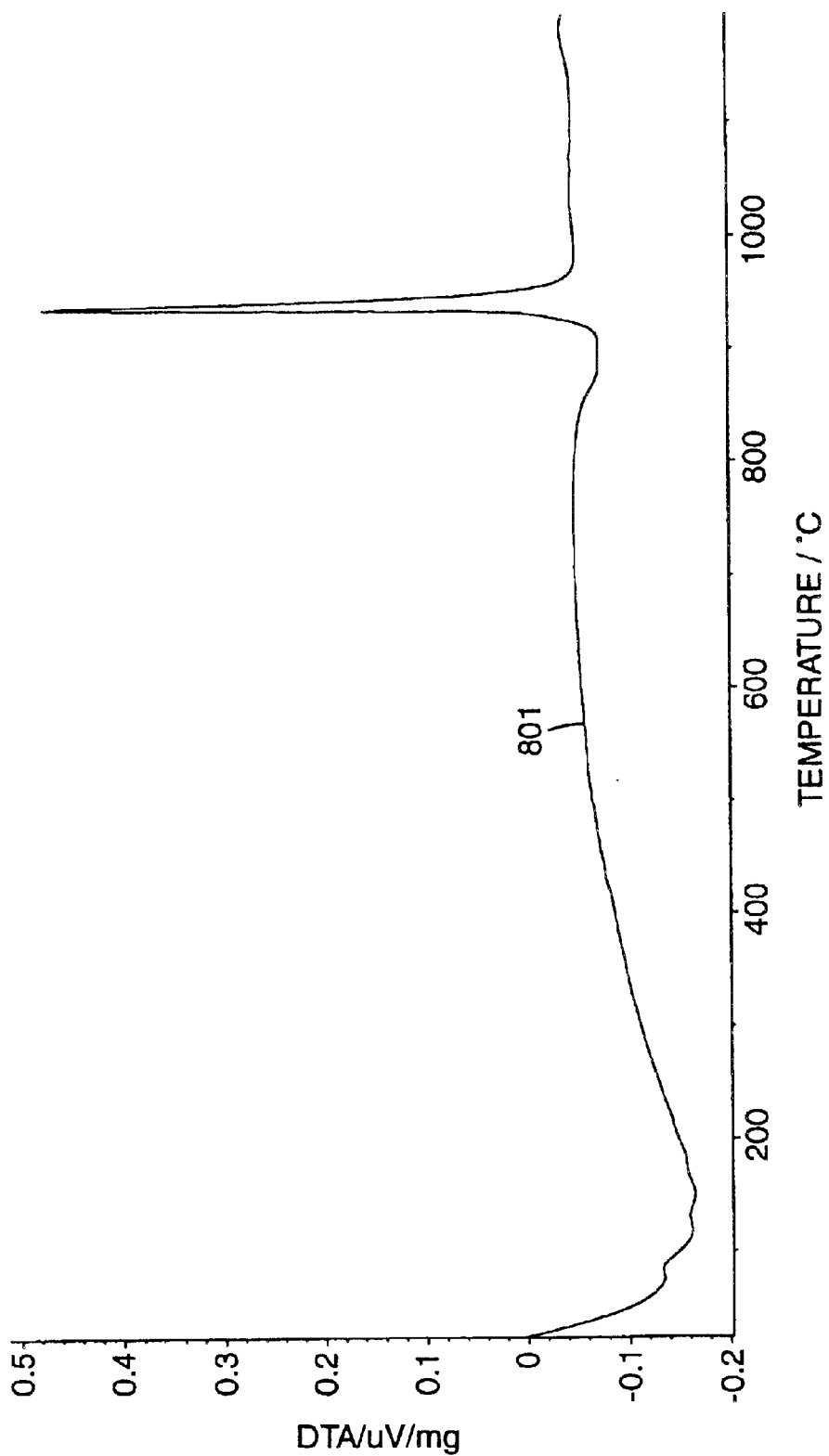
FIG. 3 is a DTA trace for Example 1 material.

Referring to FIG. 3, line 801 is the plotted DTA data for the Example 1 material. Referring to FIG. 3, line 801, the material exhibited an endothermic event at temperature around 840° C., as evidenced by the downward curve of line 801. It was believed that event was due to the glass transition ($T_g$) of the material. At about 934° C., an exothermic event was observed as evidenced by the sharp peak in line 801. It was believed that event was due to the crystallization ($T_x$) of the material. These $T_g$ and $T_x$ values for other examples are reported in Table III, above. The hot-pressing temperature at which appreciable glass flow occurred, as indicated by the displacement control unit of the hot pressing equipment described above, are reported for various examples in Table III, above. (In example 63, pressureless sintering was used.)

Example 63

About 120 g of the amorphous beads prepared as in Example 1 were placed in a graphite die and hot-pressed using uniaxial pressing apparatus (obtained under the trade designation "HP-50", Thermal Technology Inc., Brea, Calif.). The hot-pressing was carried out at 960° C. in argon atmosphere and 2 ksi (13.8 MPa) pressure to provide a hot-pressed disk. Holding time at pressure was 30 minutes.

Two cylinders were core-drilled from the hot-pressed disk and mounted on CEREC-compatible stubs; one was approximately 12 mm in diameter×15 mm in height; the other was approximately 14 mm in diameter and 17 mm in height. The lanthanum oxide/aluminum oxide/zirconium oxide material was amorphous (glassy) and dark blue in color.

Figure 4:
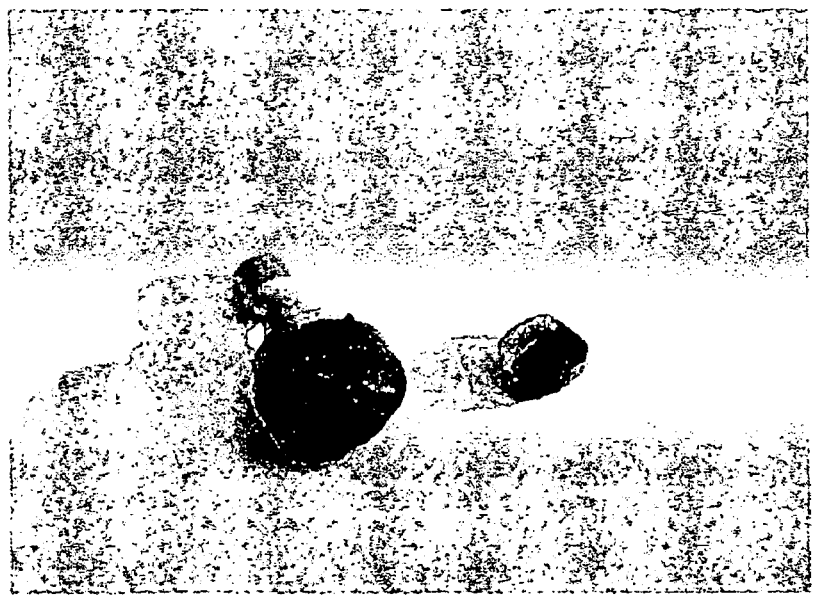
FIG. 4 is a photograph of a dental restoration milled using Example 1 material and a comparative dental restoration milled using standard (PARADIGM MZ100) material.

A dental coping was milled from the small cylinder on an automated milling system (available from Sirona Dental Systems, Bensheim, Germany, under the trade designation "CEREC 2") with LS (LabSide) software; "CEREC 2" employs a 30 mm diameter metal-plated-diamond wheel and a 1.6 mm diameter cylindrical bur. Fresh tools and lubricant water were used. The restoration was milled in under 20 minutes, and appeared similar in form to the same restoration milled in a commercial block material, PARADIGM MZ100 Block for CEREC (available from 3M Company, St. Paul, Minn.) see FIG. 4.

Example 64

A billet (approximately 37 mm in diameter and 17 mm in height) of hot-pressed lanthanum oxide/aluminum oxide/zirconium oxide material was prepared as in Example 64; a 14 mm diameter×17 mm height cylinder was core-drilled from the billlet, then prepared for the CEREC by bonding it to a CEREC stub with an epoxy adhesive (available from 3M Company, St. Paul, Minn., under the trade designation "3M DP100").

A molar full-occlusion crown was milled from the larger cylinder on the CEREC 3; a new diamond cone and 1.6-mm cylinder tools, and 100 ml of ProCAD DENTATEC Milling Additive (available from Sirona Dental Systems) in the water tank were used. The milled surface appeared identical to those of a commercial porcelain. The buccal surface was polished with a finishing brush (available from 3M Company, under the tradename, "SOF-LEX"). The resulting surface was smooth and suitable for occlusal contact.

Example 65

About 120 g of the amorphous beads prepared as in Example 1 were placed in a graphite die and hot-pressed using uniaxial pressing apparatus (obtained under the trade designation "HP-50", Thermal Technology Inc., Brea, Calif.). The hot-pressing was carried out at 960° C. in argon atmosphere and 4 ksi (27.6 MPa) pressure. Holding time at pressure was 20 minutes. The resulting disk was core drilled to make five cylindrical specimens for dental milling evaluations.

Example 66

About 50 g of the amorphous beads prepared as in Example 1 were placed in a graphite die and hot-pressed using uniaxial pressing apparatus (obtained under the trade designation "HP-50", Thermal Technology Inc., Brea, Calif.). The hot-pressing was carried out at 925° C. in argon atmosphere and 0.55 ksi (3.8 MPa) pressure. Holding time at pressure was 20 minutes. The resulting disk was core drilled to make one cylindrical specimen (approximately 10 mm in diameter×15 mm in height) for dental milling evaluations. The lanthanum oxide/aluminum oxide/zirconium oxide material was amorphous (glassy) and light yellow exhibiting some opalescence.

The block was bonded to a CEREC-compatible stub, and then machined on a CEREC 3 system (Sirona Dental Systems, Bensheim, Germany) using the set of diamond burs used in Example 65, and 75 ml of Sirona ProCAD DENTATEC lubricant in a fresh tank of deionized water. 1×4×12 mm bars were machined from the blocks. Visual inspection and the lack of error messages from the CEREC software indicated that the tools were capable of further machining. Examples 65 and 66 demonstrate that the material can be machined.

The thermal expansion behavior of Example 67 material was measured on a Seiko Thermomechanical Analyzer at a heating rate of 10° C./min. The coefficient of thermal expansion was 10.3 ppm/° C.; the softening point was about 880° C. A 10×10×3 mm disk of Example 66 material was heat-treated in a furnace (an electrically heated furnace (obtained under the trade designation "Model KKSK-666-3100" from Keith Furnaces of Pico Rivera, Calif.)) as follows. The disk was first heated from room temperature (about 25° C.) to about 900° C. at a rate of about 10° C./min and then held at 900° C. for about 1 hour. Next, the disk was heated from about 900° C. to about 1300° C. at a rate of about 10° C./min and then held at 1300° C. for about 1 hour, before cooling back to room temperature by turning off the furnace. Dimensional shrinkage that occurred during this heat-treatment was measured to be 4.5%.

Example 67

About 150 g of the amorphous beads prepared as described in Example 1 were placed in a 5 centimeter (cm)×5 cm×5 cm steel can, which was then evacuated and sealed from the atmosphere. The steel can was subsequently hot-isostatically pressed (HIPed) using a HIP apparatus (obtained under the trade designation "IPS Eagle-6", American Isostatic Presses Inc., OH). The HIPing was carried out at 207 MPa (30 ksi) pressure in an argon atmosphere. The HIPing furnace was ramped up to 970° C. at 25° C./minute and held at that temperature for 30 minutes. After the HIPing, the steel can was cut and the charge material removed. It was observed that amorphous beads had coalesced into a dense body of transparent, glassy material. The DTA trace, conducted as summarized in Examples 2–62, exhibited a glass transition ($T_g$) of 879° C. and a crystallization temperature ($T_x$) of 931° C.

Example 68

35 g of amorphous beads from Example 1, and 15 g of α-$Al_2O_3$ (obtained from Condea Vista, Tucson, Ariz., under the trade designation "APA-0.5"), were placed in a polyethylene bottle. After 80 g of distilled water and 300 g of zirconia media (Tosoh Ceramics, Bound Brook, N.J., under the trade designation "YTZ") was added to the bottle. The mixture was comminuted for 24 hours at 120 rpms. The milled material was dried using a heat gun. 20 g of the dried powder was hot-pressed as described in Example 1. The result was an opaque billet.

Example 69

20 g of amorphous beads prepared as described in Example 62, and 15 g of amorphous beads prepared as described in Example 1, were placed in an alumina crucible and heat-treated in a furnace (an electrically heated furnace (obtained under the trade designation "Model KKSK-666-3100", from Keith Furnaces of Pico Rivera, Calif.)) at 1050° C. for 1 hour. The obtained material was translucent body with beads of Example 1 evenly distributed through an amorphous matrix of viscously flowed amorphous beads of Example 62.

Example 70

15 g of amorphous beads prepared as described in Example 1 were placed in an alumina crucible and heat-treated in a furnace (an electrically heated furnace (obtained under the trade designation "Model KKSK-666-3100" from Keith Furnaces of Pico Rivera, Calif.)) at 1250° C. for 4 hours. The obtained material was easily friable but handleable body.

A 1.4 g portion of this porous, bisque-fired body was placed onto a platinum foil; 0.6 g of a lanthana-alumina-silica glass powder (VITA IN-CERAM Alumina Infiltration Glass, shade AII: Vita Zahnfabrik H. Rauter GmbH & Co. KG) was placed on top of the body. The foil, body, and glass powder were then fired in a dental porcelain furnace under vacuum at 1120° C. for 60 minutes. After firing, the body was partially infiltrated with the glass; an additional 0.93 g of glass powder was placed on the body, and then fired again per the same condition. The resulting body was fully infiltrated with the glass.

A 5×5×5 mm (0.04 g) portion of the porous, bisque-fired body was partially immersed in a tray of photocurable resin (made by mixing 20.79 parts by weight bis-GMA, 29.11 parts UDMA, 29.11 parts Bis-EMA6, 4.16 parts TEGDMA, 14.00 parts HEMA, 0.172 parts CPQ, 0.43 parts DPIHFP, 0.86 parts EDMAB, 0.086 parts BHT and 1.29 parts NOR-BLOC 7966). After two hours, the resin was fully infiltrated into the block. The block was removed and cured by exposure to light from a 3M Company XL3000 Light Cure Unit for 10 seconds, followed by two 90 second cycles in a Kulzer Dentacolor XS unit (Kulzer, Wehrheim, Germany). The result was a hard, strong, resin-ceramic composite with two interpenetrating phases.

Example 71

Plasma-Spraying

A 250-ml polyethylene bottle (7.3-cm diameter) was charged with the following 50-gram mixture: 19.3 g of alumina particles (obtained from Alcoa Industrial Chemicals, Bauxite, Ark., under the trade designation "Al6SG"), 9.5 g of zirconium oxide particles (obtained from Zirconia Sales, Inc., of Marietta, Ga. under the trade designation "DK-2"), and 21.2 g of lanthanum oxide particles (obtained from Molycorp Inc., Mountain Pass, Calif.), 75 g of isopropyl alcohol, and 200 g of alumina milling media (cylindrical in shape, both height and diameter of 0.635 cm; 99.9% alumina; obtained from Coors, Golden, Colo.). The contents of the polyethylene bottle were milled for 16 hours at 60 revolutions per minute (rpm). The ratio of alumina to zirconia in the starting material was 2:1, and the alumina and zirconia collectively made up about 58 weight percent (wt-%). After the milling, the milling media were removed and the slurry was poured onto a warm (approximately 75° C.) glass ("PYREX") pan and dried. The dried mixture was screened through a 70-mesh screen (212-micrometer opening size) with the aid of a paint brush.

After grinding and screening, the mixture of milled feed particles was fed slowly (0.5 gram/minute) into a hydrogen/oxygen torch flame to melt the particles and generate glass beads as described in Example 1. The glass beads were spherical in shape and varied in size from a few micrometers (i.e., microns) up to 250 micrometers. Subsequently, the flame-formed beads having diameters less than 125 micrometers were then passed through a plasma gun and deposited on stainless steel substrates as follows.

Four 304 stainless steel pieces (76.2 millimeter (mm)×25.4 mm×3.175 mm dimensions), and two 1080 carbon steel pieces (76.2 mm×25.4 mm×1.15 mm) were treated in the following manner. The sides to be coated were sandblasted, washed in an ultrasonic bath, and then wiped clean with isopropyl alcohol. The four 304 stainless steel and one of the 1080 carbon steel substrates were placed approximately 10 centimeters (cm) in front of the nozzle of a plasma gun (obtained under the trade designation "Praxair SG-100 Plasma Gun" from Praxair Surface Technologies, Concord, N.H.). The second 1080 carbon steel substrate was placed 18 cm in front of the nozzle of the plasma gun. The coatings made on the second 1080 carbon steel sample at a distance of 18 cm in front of the nozzle of the plasma gun were not further characterized.

The plasma unit had a power rating of 40 kW. The plasma gas was argon (50 pounds per square inch (psi), 0.3 megapascal (MPa)) with helium as the auxiliary gas (150 psi, 1 MPa). The beads were passed through the plasma gun by using argon as the carrier gas (50 psi, 0.3 MPa) using a Praxair Model 1270 computerized powder feeder (obtained from Praxair Surface Technologies, Concord, N.H.). During deposition, a potential of about 40 volts and a current of about 900 amperes was applied and the plasma gun was panned left to right, up and down, to evenly coat the substrates. When the desired thickness was achieved, the plasma spray was shut off and the samples were recovered. The 1080 carbon steel substrate was flexed, thus separating the coating from the substrate resulting in a free-standing bulk material. The deposited material had a z dimension (thickness) of about 1350 micrometers, as determined using optical microscopy.

The phase composition (glassy/amorphous/crystalline) was determined through Differential Thermal Analysis (DTA) as described below. The material was classified as amorphous if the corresponding DTA trace of the material contained an exothermic crystallization event ($T_x$). If the same trace also contained an endothermic event ($T_g$) at a temperature lower than $T_x$, it was considered to consist of a glass phase. If the DTA trace of the material contained no such events, it was considered to contain crystalline phases.

Differential thermal analysis (DTA) was conducted using the following method. DTA runs were made (using an instrument obtained from Netzsch Instruments, Selb, Germany, under the trade designation "NETZSCH STA 409 DTA/TGA") using a 140+170 mesh size fraction (i.e., the fraction collected between 105-micrometer opening size and 90-micrometer opening size screens). The amount of each screened sample placed in a 100-microliter $Al_2O_3$ sample holder was about 400 milligrams. Each sample was heated in static air at a rate of 10° C./minute from room temperature (about 25° C.) to 1100° C.

The coated material (on 304 stainless steel substrates) exhibited an endothermic event at a temperature around 880° C., as evidenced by a downward change in the curve of the trace. It is believed this event was due to the glass transition ($T_g$) of the glass material. The same material exhibited an exothermic event at a temperature around 931° C., as evidenced by a sharp peak in the trace. It is believed that this event was due to the crystallization ($T_x$) of the material. Thus, the coated material (on 304 stainless steel substrates) and the free-standing bulk material were glassy as determined by a DTA trace.

A portion of the glassy free-standing bulk material was then heat-treated at 1300° C. for 48 hours. Powder x-ray diffraction, XRD, (using an x-ray diffractometer (obtained under the trade designation "PHILLIPS XRG 3100" from Phillips, Mahwah, N.J.) with copper $K_{\alpha 1}$ radiation of 1.54050 Angstrom)) was used to determine the phases present. The phases were determined by comparing the peaks present in the XRD trace of the crystallized material to XRD patterns of crystalline phases provided in JCPDS (Joint Committee on Powder Diffraction Standards) databases, published by International Center for Diffraction Data. The resulting crystalline material included $LaAlO_3$, $ZrO_2$ (cubic, tetragonal), $LaAl_{11}O_{18}$, and transitional $Al_2O_3$ phases.

Another portion of the glassy free-standing bulk material was crystallized at 1300° C. for 1 hour in an electrically heated furnace (obtained from CM Furnaces, Bloomfield, N.J., under the trade designation "Rapid Temp Furnace"). The crystallized coating was crushed with a hammer into particles. The fraction that passed through a sieve with a 600-micrometer opening size but did not pass through a screen with 500-micrometer openings was cleaned of debris by washing in a sonic bath (obtained from Cole-Parmer, Vernon Hills, Ill., under the trade designation "8891") for 15 minutes, dried at 100° C. A portion of the particles was mounted on a metal cylinder (3 cm in diameter and 2 cm high) using carbon tape. The mounted sample was sputter coated with a thin layer of gold-palladium and viewed using a JEOL scanning electron microscopy (SEM) (Model JSM 840A). The fractured surface was rough and no crystals coarser than 200 nanometers (nm) were observed via SEM.

Example 72

Feed particles were made as described in Example 71 using the following 50-gram mixture: 21.5 g of alumina particles (obtained from Alcoa Industrial Chemicals, Bauxite, Ark. under the trade designation "Al6SG"), 9 g of zirconium oxide particles (obtained from Zirconia Sales, Inc. of Marietta, Ga. under the trade designation "DK-2"), and 19.5 g of cerium oxide particles (obtained from Rhone-Poulence, France). The ratio of alumina to zirconia in the starting material was 2.4:1 and the alumina and zirconia collectively made up about 61 weight percent. Feed particles were flame-formed into beads (of a size that varied from a few micrometers up to 250 micrometers) as described in Example 71. Subsequently, the flame-formed beads having diameters between 180 micrometers and 250 micrometers were passed through a plasma gun and deposited on stainless and carbon steel substrates as described in Example 71.

The coated 1080 carbon steel substrates were flexed, thus separating the coating from the substrate resulting in a free-standing bulk material. The resulting bulk material had a z dimension (thickness) of about 700 micrometers, as determined using optical microscopy. The microstructure was also observed using optical microscopy. The material consisted of generally spherical and oblique crystalline particles, which were opaque, within a predominantly amorphous matrix, which was transparent. Amorphous material is typically transparent due to the lack of light scattering centers such as crystal boundaries, while the crystalline particles show a crystalline structure and are opaque due to light scattering effects. The crystalline phases, determined by powder XRD analysis as described in Examples 71, consisted of $Zr_{0.4}Ce_{0.6}O_2$ (cubic) and transitional $Al_2O_3$.

A second deposition experiment was carried out using the flame-formed beads having diameters less than 125 micrometers. The resulting coating had a z dimension (thickness) of about 1100 micrometers, as determined using optical microscopy. The microstructure was also observed using optical microscopy. This material had similar features (i.e., consisted of generally spherical and oblique crystalline particles within a predominantly amorphous matrix) to those of the material formed from beads having diameters between 180 micrometers and 250 micrometers. The crystalline phases, determined by XRD analysis as described in Example 71 consisted of $Zr_{0.4}Ce_{0.6}O_2$ (cubic) and transitional $Al_2O_3$.

Example 73

Feed particles were made as described in Example 71 using the following 50-gram mixture: 27.9 g of alumina particles (obtained from Alcoa Industrial Chemicals, Bauxite, Ark. under the trade designation "Al6SG"), 7.8 g of zirconium oxide particles (obtained from Zirconia Sales, Inc., Marietta, Ga. under the trade designation "DK-2"), and 14.3 g of yttrium oxide particles (obtained from H. C. Stark Newton, Mass.). The ratio of alumina to zirconia of initial starting materials was 3.5:1 and the alumina and zirconia collectively made up about 72 weight percent. The feed particles were then screened through a 30-mesh screen (600-micrometer opening size) and heat-treated at 1400° C. for 2 hours in an electrically heated furnace (obtained from CM Furnaces, Bloomfield, N.J., under the trade designation "Rapid Temp Furnace"). The heat-treated particles were further screened to separate out particles with diameters between 125 micrometers and 180 micrometers, which were then passed through a plasma gun and deposited on stainless steel substrates as described in Example 71.

The 1080 carbon steel substrate was flexed, thus separating the coating from the substrate resulting in a free-standing bulk material. The resulting bulk material had a z dimension (thickness) of about 700 micrometers, as determined using optical microscopy. The microstructure was observed using optical microscopy. This material consisted of generally crystalline opaque particles (which retained their original shapes) within a predominantly transparent, amorphous matrix. The crystalline phases, determined by powder XRD analysis as described in Example 71, consisted of $Al_5Y_3O_{12}$ and $Y_{0.15}Zr_{0.85}O_{1.93}$.

Another portion of the free-standing bulk material was crystallized at 1300° C. for 1 hour and the fractured surface was sputter coated with a thin layer of gold-palladium and viewed using a JEOL SEM (Model JSM 840A), as described above in Example 71. The fractured surface was rough and no crystals coarser than 200 nm were observed.

Example 74

A thick coating consisting of various layers of the above three examples was plasma sprayed using feed particles produced in Examples 71–73. The first layer was coated as described in Example 72, the second as described in Example 71, and the third as described in Example 73.

The substrate was not sandblasted prior to coating so that it was removed easily by plying it apart by hand, resulting in a free-standing bulk material, approximately 75 millimeters (mm)×25 mm×7.5 mm. Cylindrical blocks were prepared by core-drilling through the thick coating.

The first layer had a z dimension (thickness) of approximately 2.5 mm, as determined using optical microscopy. The microstructure was observed using optical microscopy. This material had similar features to those of the material of Example 72 (i.e., consisted of generally spherical and opaque crystalline particles within a predominantly transparent, amorphous matrix). The second layer had a z dimension (thickness) of approximately 2 mm, as determined using optical microscopy. The microstructure was also observed using optical microscopy. This material had similar features to those of the material of Example 71 (i.e., was transparent suggesting it was amorphous). The third layer had a z dimension (thickness) of approximately 3 mm, as determined using optical microscopy. The microstructure was also observed using optical microscopy. This material had similar features to those of the material of Example 73 (i.e., it consisted of generally opaque crystalline particles (which retained their original shapes) within a predominantly transparent, amorphous matrix).

The blocks had bands of color ranging from dark umber to light beige. Two blocks (approximately 10 mm diameter× 15 mm height) were bonded to CEREC-compatible stubs, then machined on a CEREC 3 system (Sirona Dental Systems, Bensheim Germany) using a new set of diamond burs and 75 ml of Sirona ProCAD Dentatec lubricant in a fresh tank of deionized water. A molar crown was machined from one block; a coping for a maxillary lateral was machined from the other. No problems were encountered in machining. The resulting units were well machined. This example demonstrates that a plasma-sprayed embodiment of the invention can be made and machined, and also a multicolored block can be made.

Example 75

Nanoparticulates of $La_2O_3$—$Al_2O_3$—$ZrO_2$ (LAZ) and $CeO_2$—$Al_2O_3$—$ZrO_2$ (CAZ) materials the compositions shown in Table IV were prepared according to the method disclosed in U.S. Pat. No. 5,958,361 (Laine et al).

TABLE IV

| Material | $CeO_2$ | $La_2O_3$ | $Al_2O_3$ | $ZrO_2$ |
| --- | --- | --- | --- | --- |
| LAZ | NA | 42.50 | 38.75 | 18.75 |
| CAZ | 39.00 | NA | 43.00 | 18.00 |

Other processes such as those described in U.S. Pat. Nos. 5,075,090, (Lewis et al) and 5,358,695 (Helble et al) can also be used to produce particulates useful in this example.

Powder x-ray diffraction, XRD, (using an x-ray diffractometer (obtained under the trade designation "PHILLIPS XRG 3100" from Phillips, Mahwah, N.J.) with copper $K_{\alpha 1}$ radiation of 1.54050 Angstrom) was used to determine the phases present. The phases were determined by comparing the peaks present in the XRD trace of the crystallized material to XRD patterns of crystalline phases provided in JCPDS (Joint Committee on Powder Diffraction Standards) databases, published by International Center for Diffraction Data. The resulting phases are reported in Table V.

TABLE V

XRD Analysis of Crystalline Phases

| | Identified Phases/Relative Intensities |
|---|---|
| $La_2O_3$—$Al_2O_3$—$ZrO_2$ (LAZ) | Amorphous + $LaAlO_3$ ($D_{app}$ = 580 Å)/100 + "$La_{0.25}Zr_{0.75}O_{1.875}$"/37 + transitional $Al_2O_3$/18 |
| $CeO_2$—$Al_2O_3$—$ZrO_2$ | "$Zr_{0.4}Ce_{0.6}O_2$" (cubic, $a_0 \approx 5.30$ Å) ($D_{app}$ = 240 Å)/100 + transitional $Al_2O_3$/6 + (possible $CeAlO_3$)/5 |

5.570 g of LAZ powder was treated with 5.570 g of a silane agent (3M Company RELY X Ceramic Primer), allowed to dry; 3.618 g of the resulting powder was then blended with 2.59 g of the photocurable resin made by blending 24.18 parts by weight of bis-GMA, 33.85 parts UDMA, 33.85 parts bis-EMA6, 4.84 parts TEGDMA, 0.2 parts CPQ, 0.5 parts DPHFP, 1.0 parts EDMAB, 0.1 parts BHT, and 1.5 parts of NORBLOCK 7966. The resulting composite was white in color and had viscosity and handling suitable for a flowable style dental composite. The composite was filled into a mold 2 mm deep by 5 mm diameter, in two increments of 1 mm, each cured for 60 seconds with a 3M Company XL3000 Dental Curing Light. The hardness of the cured composite was measured with a Barcol Hardness meter, models GYZJ-934-1 (Barber Coleman, Inc., Loves Park, Ill.). An average Barcol Hardness of 91±0.6 was measured on the top surface of the cured composite.

An intracoronal inlay on a molar tooth was prepared in a gypsum dental model. The composite was loaded into the preparation in several 1-mm increments, each cured for 60 seconds with a 3M Company XL3000 Dental Curing Light; in the final increment, occlusal anatomy was sculpted into the composite before curing. The resulting inlay was esthetic.

Example 76

84.9 g of aluminum formoacetate were charged to a Pyrex beaker, which was then placed on a hotplate/stirred with a Teflon-coated stir bar; 16.5 g of zirconyl acetate (Magnesium Elektron Inc.) were added under vigorous stirring to form a clear, slightly turbid sol, followed by 22.5 g of lanthanum nitrate (Johnson Matthey #12915, 99.9%). The ingredients blended readily to form a clear, slightly turbid, opalescent sol with no precipitates, gelation, or thickening, suitable for further processes such as flame-spraying, spray-drying, coating, spray pyrolysis, gelation/drying/calcinations, gelation/autoclaving, or controlled precipitation of particles. The sol was calculated to have a nominal yield of 20 g of oxide of composition $La_2O_3$ 42.3 wt-%, $Al_2O_3$ 39.2 wt-%, $ZrO_2$ 18.5 wt-%. 9.1 g of polyethylene glycol MW=400 ($PEG_{400}$: Union Carbide Carbowax, Sentry Grade) was added to the sol; a small vial of this PEG-doped sol was saved to observe stability. This sol was stable for 8 hours, but developed white gel precipitates after 24 hours. To the remaining sol was added 10.8 g of the liquid component of VITREMER CORE Restorative liquid (available from 3M Company, St. Paul, Minn.), which formed a soft solid mass in 3 hours. This soft solid mass was dried at 100° C./5 hrs. TG/DTA analysis of the dried material showed weight loss below about 500° C. due to water evaporation and pyrolysis of the organics and nitrates/acetates. Exotherm peaks at 208° C. and 372° C. are due to the pyrolysis. Surprisingly, there were no endotherms from crystallization up to as high as 1300° C.; the resulting powder was white. Samples of the dried sol were calcined at 550° C./4 hr and 850° C./4 hr; the results (Table VI) show a large amorphous portion, and some crystalline phases.

TABLE VI

XRD Results

| Description | Identified Phases/Relative Intensities |
|---|---|
| LAZ sol-gel, calcined at 550° C.; Grey, granular powder | $La_2O_2CO_3$/100 + $La_2CO_5$/65 + amorphous |
| LAZ sol-gel, calcined at 850° C.; Off-white, granular powder | $La_2O_3$/100 + $La(OH)_3$/52 + $LaAlO_3$/48 + amorphous |

2.90 g of the powder was treated with 2.9 g of a silane agent (3M Company RELYX Ceramic Primer), allowed to dry, and then blended with 2.9 g of photocurable resin (made by blending 24.18 parts by weight bis-GMA, 33.85 parts UDMA, 33.85 parts Bis-EMA6, 4.84 parts TEGDMA, 0.2 parts CPQ, 0.5 parts DPHFP, 1.0 parts EDMAB, 0.1 parts BHT and 1.5 parts NORBLOC 7966)). The resulting composite was ivory in color and had viscosity and handling suitable for a flowable style dental composite. The composite was filled into a mold 2 mm deep by 5 mm diameter, in two increments of 1 mm, each cured for 60 seconds with a 3M Company XL3000 Dental Curing Light. The hardness of the cured composite was measured with a Barcol Hardness meter, models GYZJ-934-1 (Barber Coleman, Inc., Loves Park, Ill.). An average Barcol Hardness of 91+1 was measured on the top surface of the cured composite.

Example 77

42.6 parts by weight (pbs) of aluminum formoacetate were charged to a Pyrex beaker, which was then placed on a hotplate/stirred with a Teflon-coated stir bar; 8.3 pbw of zirconyl acetate (Magnesium Elektron Inc.) were added under vigorous stirring, followed by 11.3 pbw of lanthanum nitrate (Johnson Matthey #12915, 99.9%), then 0.6 pbw of polyethylene glycol MW=400 ($PEG_{400}$: Union Carbide Carbowax, Sentry Grade), and sufficient nitric acid to reduce the pH from ~4.4 to ~3–3.3. The ingredients blended readily to form a clear, slightly turbid, opalescent sol with no precipitates, gelation, or thickening, suitable for further processes such as flame-spraying, spray-drying, coating, spray pyrolysis, gelation/drying/calcinations, gelation/autoclaving, or controlled precipitation of particles. The sol was calculated to have a composition $La_2O_3$ 42.3 wt-%, $Al_2O_3$ 39.2 wt-%, $ZrO_2$ 18.5 wt-%. The sol was spray-dried immediately after mixing to a fine, free-flowing powder in a Buchi spray dryer. TG/DTA analysis of the dried material shows weight loss below circa 500° C. due to water evaporation and pyrolysis of the organics and nitrates/acetates. An exotherm peaks at 100.7° C. can be attributed to water evaporation, and 348.7° C. to the pyrolysis of the organics. Surprisingly, there are no endotherms from crystallization up to as high as 1300° C.; the resulting powder was white.

A small sample of an identically blended sol was retained to observe stability; another small sample was diluted with water by mixing 2.3 g of sol and 1.7 g deionized water. Both sols were stable at 15 hr; the undiluted sol developed a fine layer of white precipitate by circa 40 hours, while the diluted sol was free of precipitates, gelation, or thickening after 5 days.

A sample of this powder was calcined at 550° C. for 1 hour in air (resultant powder was white) and hot-pressed at 970° C. as described in Example 1; XRD on resulting semi-solid disk showed that the major crystalline phase present was a face-centered cubic (FCC) crystal structure with a lattice parameter of ~5.28 Å, most likely due to a stabilized form of zirconia. A possible transitional alumina phase was also observed, as well as an unidentified phase(s) with diffraction peaks at d-spacings of ~4.1 Å and ~3.7 Å. The powder was then fired at 700° C./4 hr; the resulting white powder was crushed in a mortar and pestle.

Example 78

84.9 g of aluminum formoacetate were charged to a PYREX beaker, which was then placed on a hotplate/stirrer with a Teflon-coated stir bar; 16.6 g of zirconyl acetate were added under vigorous, followed by 87.3 g deionized water, 22.5 g of lanthanum nitrate hexahydrate, 1.8 g polyethylene glycol (MW=400), and 3.6 g nitric acid. The ingredients blended readily to form a clear, slightly turbid, opalescent sol with no precipitates, gelation, or thickening, suitable for further processes such as flame-spraying, spray-drying, coating, spray pyrolysis, or controlled precipitation. The sol was calculated to have a nominal yield of 42.3 wt-% $La_2O_3$, 39.2% $Al_2O_3$, and 18.5% $ZrO_2$.

The sol was applied to the following substrates with a cotton swab:

A. glass slide: 1 coat, dry in air
B. glass slide: 1 coat, dry with compressed air
C. glass slide: 4 coats, dried in air between coats
D. opaque aluminum oxide wafer: 1 coat, dry in air
E. translucent alumina wafer: 1 coat, dry in air
F. translucent alumina wafer: 1 coat, dry in air (thicker layer)
G. glass slide: swipe several lines, dry in air The coated substrates were fired at 550° C./2 hr. Samples (B), (E), (G) were clear and well-bonded; the others were black and flaky. The remaining sol was stored under ambient storage conditions in a sealed vial; after 13 days the sol remained free of precipitates, gelation, separation, or thickening.

Example 79

The samples of Example 78 were additionally fired at 560° C. for 8 hours. On samples where the brushed sol coating was thick, the fired coating was dark brown and could be rubbed off; on samples where the brushed sol coating was thin (because of compressed air drying, or barely-wet brush), the coating was clear and well-bonded. The sol has been stable for 13 days to date, with no precipitates, gelation, or thickening.

The complete disclosures of the patents, patent documents, and publications cited herein are incorporated by reference in their entirety as if each were individually incorporated. Various modifications and alterations to this invention will become apparent to those skilled in the art and are foreseeable without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An article comprising at least one of a glass or glass-ceramic comprising:

a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;

b) at least 35 percent by weight $Al_2O_3$, based on the total weight of the glass or glass-ceramic, and a first metal oxide other than $Al_2O_3$, wherein the $Al_2O_3$ and the first metal oxide collectively comprise at least 70 percent by weight of the glass or glass-ceramic;

c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;

d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;

e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;

f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;

g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;

h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or i) a glass-ceramic having an average hardness of at least 13 GPa, wherein the glass-ceramic has x, y, and z dimensions each perpendicular to each other, and wherein each of the x, y, and z dimensions is at least 5 mm, and wherein said article is in the form of a dental article or orthodontic appliance.

2. The article of claim 1 wherein the dental article is selected from the group consisting of restoratives, replacements, inlays, onlays, veneers, full and partial crowns, bridges, implants, implant abutments, copings, anterior fillings, posterior fillings, and cavity liner, and bridge frameworks.

3. The article of claim 1 wherein the orthodontic appliance is selected from the group consisting of brackets, buccal tubes, cleats, and buttons.

4. A kit comprising a plurality of orthodontic or dental components, wherein at least one of the components includes a dental material, dental article, or an orthodontic appliance which comprises a glass or glass-ceramic comprising:
- a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;
- b) at least 35 percent by weight $Al_2O_3$, based on the total weight of the glass or glass-ceramic, and a first metal oxide other than $Al_2O_3$, wherein the $Al_2O_3$ and the first metal oxide collectively comprise at least 70 percent by weight of the glass or glass-ceramic;
- c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;
- d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;
- e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;
- f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;
- g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;
- h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or
- i) a glass-ceramic having an average hardness of at least 13 GPa.

5. The kit of claim 14 further comprising a component selected from the group consisting of an orthodontic adhesive, an adhesive primer, an appliance-positioning tool, and combinations thereof.

6. The kit of claim 14 further comprising a component selected from the group consisting of a dental mill blank, a bonding agent, a milling lubricant, a color-matching composition suitable for using in an oral environment, an impression material, an instrument, a dental composite, a dental porcelain, an abrasive, and combinations thereof.

7. A method of performing a dental restoration comprising the steps of:
preparing a dental site to be restored; and
applying a restorative material comprising a glass or glass-ceramic comprising at least one of:
- a) at least 35 percent by weight $Al_2O_3$, based on the total weight of the glass or glass-ceramic, and a first metal oxide other than $Al_2O_3$, wherein the glass or glass-ceramic contains not more than 10 percent by weight collectively $B_2O_3$, $GeO_2$, $P_2O_5$, $SiO_2$, $TeO_2$, and $V_2O_5$, based on the total weight of the glass or glass-ceramic;
- b) at least 35 percent by weight $Al_2O_3$, based on the total weight of the glass or glass-ceramic, and a first metal oxide other than $Al_2O_3$, wherein the $Al_2O_3$ and the first metal oxide, collectively comprise at least 70 percent by weight of the glass or glass-ceramic;
- c) $Al_2O_3$ and at least one of REO or $Y_2O_3$, wherein at least 80 percent by weight of the glass or glass-ceramic collectively comprises the $Al_2O_3$ and the at least one of REO or $Y_2O_3$, based on the total weight of the glass or glass-ceramic;
- d) $Al_2O_3$, at least one of REO or $Y_2O_3$, and at least one of $ZrO_2$ or $HfO_2$, wherein at least 80 percent by weight of the glass or glass-ceramic collectively comprises the $Al_2O_3$, at least one of REO or $Y_2O_3$, and at least one of $ZrO_2$ or $HfO_2$, based on the total weight of the glass or glass-ceramic;
- e) $Al_2O_3$ and at least one of REO or $Y_2O_3$, wherein at least 60 percent by weight of the glass or glass-ceramic collectively comprises the $Al_2O_3$ and the at least one of REO or $Y_2O_3$, and wherein the glass or glass-ceramic contains not more than 20 percent by weight $SiO_2$ and not more than 20 percent by weight $B_2O_3$, based on the total weight of the glass or glass-ceramic;
- f) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 20 percent by weight $SiO_2$ and not more than 20 percent by weight $B_2O_3$, based on the total weight of the glass or glass-ceramic;
- g) $Al_2O_3$ and at least one of REO or $Y_2O_3$, wherein at least 60 percent by weight of the glass or glass-ceramic comprise the $Al_2O_3$ and the at least one of REO or $Y_2O_3$, and wherein the glass or glass-ceramic contains not more than 40 percent by weight collectively $SiO_2$, $B_2O_3$, and $P_2O_5$, based on the total weight of the glass or glass-ceramic;
- h) $Al_2O_3$, at least one of REO or $Y_2O_3$, and at least one of $ZrO_2$ or $HfO_2$, wherein at least 60 percent by weight of the glass or glass-ceramic collectively comprises the $Al_2O_3$, at least one of REO or $Y_2O_3$, and at least one of $ZrO_2$ or $HfO_2$, and wherein the glass or glass-ceramic contains not more than 40 percent by weight collectively $SiO_2$, $B_2O_3$, and $P_2O_5$, based on the total weight of the glass or glass-ceramic; or
- i) a glass-ceramic having an average hardness of at least 13 GPa.

8. The method of claim 7 wherein the restorative material is selected from the group consisting of veneers, crowns, inlays, onlays, and bridge structures.

* * * * *

UNITED STATES PATENT AND TRADEMARK OFFICE
CERTIFICATE OF CORRECTION

| | | |
|---|---|---|
| PATENT NO. | : 6,984,261 B2 | Page 1 of 3 |
| APPLICATION NO. | : 10/358856 | |
| DATED | : January 10, 2006 | |
| INVENTOR(S) | : Kevin M. Cummings | |

It is certified that error appears in the above-identified patent and that said Letters Patent is hereby corrected as shown below:

Title page,

Item (56), References Cited, U.S. Patent Documents, Page 2,
delete
"3,629,187 A 12/1971 Walier" and insert in place thereof
-- 3,629,187 A 12/1971 Waller --.

Item (56), References Cited, Other Publications, Page 3, delete
" "Durable 3-5 µm transmitting infrared window materials" Harris, ELSEVIER, Infrared Physics & Technology, 39, 1998, pp. 185-201." and
insert in place thereof -- "Durable 3-5 µm transmitting infrared window materials", Harris, ELSEVIER, Infrared Physics & Technology, 39, 1998, pp. 185-201. --.

Item (56), References Cited, Other Publications, Page 3, delete
" "Eutectic Precipitation of the Spinel Solid Solution-Yttriu-m-
Aluminum Garnet (YAG) System," Wang et al., J. Am. Ceram. Soc., 81 [1], 1998, pp. 263-265." and insert in place thereof -- "Eutectic Precipitation of the Spinel Solid Solution-Yttrium Aluminum Garnet (YAG) System.," Wang et al., J. Am. Ceram. Soc., 81 [1], 1998, pp. 263-265. --.

Item (56), References Cited, Other Publications, Page 3, delete " "Increase in value of rare-earth products boosts Yixing Xinwei", South China Morning Post, April 12, 2000" and insert in place thereof
-- "Increase in value of rare-earth products boosts Yixing Xinwei", Yau, South China Morning Post, April 12, 2000. --.

Item (56), References Cited, Other Publications, Page 3, delete " "Interface modification for increased fracture toughness in reaction formed yttrium aluminum garnet/alumina eutectic composites," Brewer et al., J. Mater. Res., Vol. 14, No. 10, October 1999, pp. 3907-3912." and insert in place thereof -- "Interface modification for increased fracture toughness in reaction-formed yttrium aluminum garnet/alumina eutectic composites," Brewer et al., J. Mater. Res., Vol. 14, No. 10, October1999, pp. 3907-3912. --.

Item (56), References Cited, Other Publications, Page 4, delete " "Rare earth oxide-aluminum oxide glasses for mid range IR devices", Weber et al., Containerless Research, Inc. (Believed to be presented at Bios 2003 Conference, 26 January 2003)" and insert in place thereof
-- "Rare earth oxide-aluminum oxide glasses for mid-range IR devices", Weber et al., Containerless Research, Inc. (Believed to be presented at Bios 2003 Conference, 26 January 2003). --.

UNITED STATES PATENT AND TRADEMARK OFFICE
CERTIFICATE OF CORRECTION

PATENT NO. : 6,984,261 B2
APPLICATION NO. : 10/358856
DATED : January 10, 2006
INVENTOR(S) : Kevin M. Cummings It is certified that error appears in the above-identified patent and that said Letters Patent is hereby corrected as shown below:

Title Page (cont'd),

Item (56), References Cited, Other Publications, Page 4, delete "U.S. Appl. No. 10/211,638, filed Aug. 2, 2000, $Al_2O_3$-$Y_2O_3$-$ZrO_2$/$HfO_2$ Materials, and Methods of Making and Using the Same." and insert in place thereof -- U.S. Appl. No. 10/211,638, filed Aug. 2, 2002, $Al_2O_3$-$Y_2O_3$-$ZrO_2$/$HfO_2$ Materials, and Methods of Making and Using the Same. -- .

Column 7
Line 53, delete "$MgA_{l2}O_4$," and insert in place thereof -- $MgAl_2O_4$,--
Line 57, delete "$MgA_{l2}O_4$," and insert in place thereof -- $MgAl_2O_4$,--

Column 14,
Line 7, delete "$Al_2O_3$ metal" and insert in place thereof --$Al_2O_3 \cdot$metal --.

Column 19,
Line 59, delete "LaAl11$O_{18}$," and insert in place thereof -- $LaAl_{11}O_{18}$, --.
Line 65, delete "$Al_2O_3$ metal" and insert in place thereof -- $Al_2O_3 \cdot$metal --.

Column 22,
Line 44, delete "abandoned," and insert in place thereof -- abandoned; --.
Line 47, delete "2003:" and insert in place thereof -- 2003; --.

Column 33,
Line 62, delete "Materials'" and insert in place thereof -- Materials --.

UNITED STATES PATENT AND TRADEMARK OFFICE
CERTIFICATE OF CORRECTION

PATENT NO. : 6,984,261 B2
APPLICATION NO. : 10/358856
DATED : January 10, 2006
INVENTOR(S) : Kevin M. Cummings It is certified that error appears in the above-identified patent and that said Letters Patent is hereby corrected as shown below:

<u>Column 53,</u>
Line 58, delete "claim 14" and insert in place thereof -- claim 4 --.
Line 62, delete "claim 14" and insert in place thereof -- claim 4 --.

Signed and Sealed this

Twelfth Day of June, 2007

JON W. DUDAS
*Director of the United States Patent and Trademark Office*